(12) United States Patent
Klinger et al.

(10) Patent No.: US 8,759,314 B2
(45) Date of Patent: *Jun. 24, 2014

(54) METHODS FOR TREATING MULTIPLE SCLEROSIS USING ANTISENSE OLIGONUCLEOTIDES

(71) Applicants: Ety Klinger, Tzahala (IL); Shoshi Tessler, Zichron Yaaqov (IL); Hallak Hussein, Jerusalem (IL); George Tachas, Melbourne (AU); Mark Paul Diamond, Melbourne (AU)

(72) Inventors: Ety Klinger, Tzahala (IL); Shoshi Tessler, Zichron Yaaqov (IL); Hallak Hussein, Jerusalem (IL); George Tachas, Melbourne (AU); Mark Paul Diamond, Melbourne (AU)

(73) Assignees: Antisense Therapeutics Limited, Victoria (AU); Teva Pharmaceutical Industries, Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,811

(22) Filed: Mar. 22, 2013

(65) Prior Publication Data

US 2013/0345293 A1    Dec. 26, 2013

Related U.S. Application Data

(63) Continuation of application No. 12/456,883, filed on Jun. 23, 2009, now Pat. No. 8,415,314.

(60) Provisional application No. 61/132,973, filed on Jun. 23, 2008.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ..................... 514/44 A; 536/24.5

(58) Field of Classification Search
USPC ........................ 514/44; 536/24.5
See application file for complete search history.

(56) References Cited

U.S. PATENT DOCUMENTS

| 6,242,591 | B1 | 6/2001 | Cole et al. |
| 6,258,790 | B1 | 7/2001 | Bennett et al. |
| 8,415,314 | B2 * | 4/2013 | Klinger et al. .............. 514/44 A |
| 2007/0237717 | A1 | 10/2007 | Martin et al. |
| 2010/0119480 | A1 | 5/2010 | Klinger et al. |

FOREIGN PATENT DOCUMENTS

| WO | WO 00/20635 | 4/2000 |
| WO | WO 2006/086821 | 8/2006 |
| WO | WO 2010/008474 A3 | 1/2010 |

OTHER PUBLICATIONS

International Search Report issued in connection with PCT International Application No. PCT/US2009/003760 (WO 2010/008747 A3) published Jan. 21, 2010 (Klinger et al.).
van Oosten B.W. et al. (1997) "Treatment of multiple sclerosis with the monoclonal anti-CD4 antibody cM-T412: Results of a randomized, double-blind, placebo-controlled, MR-monitored phase II trial" Neurology 49:351-357.

(Continued)

*Primary Examiner* — Terra Cotta Gibbs
(74) *Attorney, Agent, or Firm* — John P. White; Cooper & Dunham LLP

(57) ABSTRACT

A method for treating a patient suffering from multiple sclerosis, particularly a relapsing form of multiple sclerosis, comprising periodically administering a pharmaceutical composition comprising a therapeutically effective amount of OLIGONUCLEOTIDE 1 to the patient, thereby treating the patient.

31 Claims, 11 Drawing Sheets

(56) References Cited

OTHER PUBLICATIONS

Steinman L. (2005) "Blocking Adhesion Molecules as Therapy for Multiple Sclerosis: Natalizumab" Nature 4:510-518.

Rovira A. and Leon A. (2008) "MR in the diagnosis and monitoring of multiple sclerosis: An overview" European Journal of Radiology 67:409-414.

Kerlero de Rosbo N. et al. (1993) "Reactivity to Myelin Antigens in Multiple Sclerosis" J. Clin. Invest. 92:2602-2608.

Kerlero de Rosbo N. and Ben-Nun A. (1998) "T-cell Responses to Myelin Antigens in Multiple Sclerosis; Relevance of the Predominant Autoimmune Reactivity to Myelin Oligodendrocyte Glycoprotein" Journal of Autoimmunity 11:287-299.

Pender M.P. et al. (2000) "Surges of Increased T Cell Reactivity to an Encephalitogenic Region of Myelin Proteolipid Protein Occur More Often in Patients with Multiple Sclerosis Than in Healthy Subjects" J. Immunol. 165:5322-5331.

Pelfrey C.M. et al. (1996) "T cell response to two immunodominant proteolipid protein (PLP) peptides in multiple sclerosis patients and healthy controls" Multiple Sclerosis 1:270-278.

Van Noort J.M. et al. (1995) "The small heat-shock protein αB-cryltallin as candidate autoantigen in multiple sclerosis" Nature 375:798.

Medizinfo, Multiple Skerose. Epidemiologie. Available from URL: www.medizinfo.de/kopfundseele/multipleklerose/msept.htm, downloaded Jan. 5, 2010.

The Merk Manual of Medical Information, Second Home Edition; Blood Disorder, Bleeding and Clotting Disorders. www.merck.com/mmhe/print/sec14/ch173/ch173.html, Last full review/revision May 2006 by Joel L. Moake, MD.

McDonald W.I. et al. (2001) "Recommended Diagnostic Criteria for Multiple Sclerosis: Guidelines from the International Panel on the Diagnosis of Multiple Sclerosis" Ann. Neurol. 50:121-127.

Jen K.Y. and Gewirtz A.M. (2000) "Suppression of Gene Expression by Targeted Disruption of Messenger RNA:Available Options and Current Strategies" Stem Cells 18:307-319.

Johnson D. et al. (1986) Cell-Mediated Immunity to Myelin-Associated Glycoprotein, Proteolipid Protein, and Myelin Basic Protein in Multiple Sclerosis Journal of Neuroimmunology 13:99-108.

Helene C. and Toulme J.J. (1990) "Specific regulation of gene expression by antisense, sense and antigene nucleic acids" Biochimica et Biophysica Acta 1049:99-125.

Frohman E.M. et al. (2003) "The utility of MRI in suspected MS" Neurology 61:602-611.

Diaz-Villoslada P. et al. (1999) "Autoreactivity to myelin antigens: myelins/oligodendrocyte glycoprotein is a prevalent autoantigen" Journal of Neuroimmunology 99:36-43.

Cutter G.R. et al. (1999) "Development of a multiple sclerosis functional composite as a clinical trial outcome measure" Brain 122:871-882.

Crooke S.T. (1993) "Progress toward Oligonucleotide therapeutics: pharmacodynamic proterties" The FASEB Journal 7:533-539.

Crooke S.T. (1992) "Therapeutic Applications of Oligonucleotides" Annu. Rev. Pharmacol. Toxicol. 32:329-76.

CPMP—Committee for Proprietary Medicinal Products. "Note for Guidance on Good Clinical Practice" Londong, Jan. 1997; CPMP/ICH/135/95:1-58.

CPMP—Committee for Proprietary Medicinal Products. "Note for Guidance on Clinical Investigation of Medicinal Products for the Treatment of Multiple Sclerosis" London, Jul. 28, 1999; CPMP/EWP/561/98:1-10.

Cohen J.S. (1991) "Antisense oligodeoxynucleotides as antiviral agents" Antiviral Research 16:121-133.

Chou Y.K. et al. (1992) "Frequency of T cells specific for myelin basic protein and myelin proteolipid protein in blood and celebrospinal fluid in multiple sclerosis" Journal of Neuroimmunology 38:105-114.

Calabretta B. (1991) "Inhibition of Protooncogene Expression by Antisense Oligodeoxynucleotides: Biological and Therapeutic Implications" Cancer Research 51:4505-4510.

Brex P.A. et al. (2002) "A longitudinal study of abnormalities on MRI and disability from multiple sclerosis" N. Engl. J. Med. 346:158-164.

Teva & ANP Announce That ATL/TV1102, A Novel Drug for the Treatment of Relapsing Remitting Multiple Sclerosis (RRMS), Demonstrated Signigicant Reduction in Disease Activity, www.tevapharm.com, Jun. 29, 2008.

Natalizumb label FDA document I61061-1 (Nov. 2004).

EMEA Natalizumab Scientific Discussion European Public Assessment Report (EPAR) (2006).

Natalizumab label FDA document I61061-4 (Jan. 2008).

Gold et al., (2006), "Understanding pathogenesis and therapy of multiple sclerosis via animal models: 70 years of merits and culprits in experimental autoimmune encephalomyelitis research," Brain, 129, pp. 1953-1971.

International Preliminary Report on Patentability issued Jan. 5, 2011 in connection with PCT International Application No. PCT/US2009/003760 (WO 2010/008474 A3) (Klinger et al.).

Antisense Therapeutics (Jul. 28, 2004) Investor Update. Further Marker Developments re Treatments for Multiple Sclerosis.

O'Connor, (2007) "Natalizumab and the role of $\alpha_4$-integrin antagonism in the treatment of multiple sclerosis" Expert Opin. Biol. Ther. 7(1):123-136.

Sep. 9, 2010 Response filed in connection with U.S. Appl. No. 12/456,883.

Dec. 9, 2010 Office Action, issued in connection with U.S. Appl. No. 12/456,883.

Jun. 9, 2011 Response filed in connection with U.S. Appl. No. 12/456,883.

Aug. 25, 2011 Office Action, issued in connection with U.S. Appl. No. 12/456,883.

Feb. 27, 2012 Response filed in connection with U.S. Appl. No. 12/456,883.

Dec. 10, 2012 Notice of Allowance, issued in connection with U.S. Appl. No. 12/456,883.

Sriram and Steiner, (2005) "Experimental Allergic Encephalomyelitis: A Misleading Model of Multiple Sclerosis" Ann Neurol 58:939-945.

Tubridy et al. (1999) "The effect of anti-[alpha]4 integrin antibody on brain lesion activity in MS" Neurology 53(3):466-472.

First Examination Report issued on May 1, 2013 in connection with corresponding Australian application 2009271678.

Response to First Examination Report filed on Jul. 26, 2013 in connection with corresponding Australian application 2009271678.

Second Examination Report issued on Aug. 5, 2013 in connection with corresponding Australian application 2009271678.

Response to Second Examination Report filed on Aug. 29, 2013 in connection with corresponding Australian application 2009271678.

Extended European Search Report issued on Nov. 27, 2012 in connection with corresponding European application 09798248.2.

Response to Extended European Search Report filed on Aug. 5, 2013 for corresponding European application 09798248.2.

First Examination Report issued on Sep. 19, 2013 in connection with corresponding European application 09798248.2.

English Language Translation of First Examination Report issued on Nov. 26, 2013 in connection with corresponding Japanese application 2011-516297.

Coisne et al. (2007) "Therapeutic Targeting of Leukocyte Trafficking Across the Blood-Brain Barrier" Inflammation & Allergy Drug Targets 6(4):210-222.

Corey (2007) "RNA learns from antisense" Nature Chemical Biology 3(1):8-11.

Godfray et al. (2004) "The use of nucleic acid tools for target validation in central nervous system therapy" Drug Discovery Today 1(2):85-91.

(56) References Cited

OTHER PUBLICATIONS

Limmroth et al. (2009) "VLA-4 Antisense—An Oligonucleotide Targeting VLA-4 mRNA (ATL1102) Significantly Reduces New Active Lesions in Patients with RR-MS" Neurology 72(11), suppl. 3:A112.

Mealy et al. (2004) Drugs of the Future, vol. 29, No. 3, pp. 265.

The Merk Manuals online medical library [online], 2005, [Search date: Nov. 13, 2013], available at merckmanual.jp/mmpej/print/sec16/ch222/ch222b.html (as translated into the English Language by Google Translator).

Miller et al. (2003) "A Controlled Trial of Natalizumab for Relapsing Multiple Sclerosis" The New England Journal of Medicine, vol. 348, No. 1, p. 15-23.

Myers et al. (2005) "Antisense oligonucleotide blockade of alpha 4 integrin prevents and reverses clinical symptoms in murine experimental autoimmune encephalomyelitis." Journal of Neuroimmunology 160(1-2):12-24.

Osawa, (2004) Modern Physician, vol. 24, No. 12, p. 1853-1855.

Rayburn et al. (2008) "Antisense, RNAi, and gene silencing strategies for therapy: Mission possible or impossible?" Drug Discovery Today 13(11-12):513-521.

Tafech et al. (2006) "Destroying RNA as a Therapeutic Approach" Current Medicinal Chemistry 13(8):863-881.

\* cited by examiner

A.

B.

C.

A.

B.

A.

B.

C.

A.

B.

A.

B.

METHODS FOR TREATING MULTIPLE SCLEROSIS USING ANTISENSE OLIGONUCLEOTIDES

This application is a continuation of U.S. Ser. No. 12/456,883, filed Jun. 23, 2009, now U.S. Pat. No. 8,415,314, issued Apr. 9, 2013, claiming benefit of U.S. Provisional Patent Application Ser. No. 61/132,973 filed Jun. 23, 2008, the contents of each of which are hereby incorporated by reference herein.

Throughout this application various publications are referenced by Arabic numeral in parentheses. The full citation of the corresponding reference appears at the end of the specifications before the claims. The disclosures of these publications in their entireties are hereby incorporated by reference into this application in order to more fully describe the state of the art to which this invention pertains.

FIELD AND BACKGROUND OF THE INVENTION

The present invention relates to methods of treating Multiple Sclerosis, particularly Relapsing forms of Multiple Sclerosis.

Multiple Sclerosis

Multiple Sclerosis (MS) is a common neurological disease affecting more than 1 million people worldwide. Its prevalence rate varies between races and geographical latitude, ranging from more than 100 per 100,000 in Northern and Central Europe to 50 per 100,000 in Southern Europe. MS is the most common cause of neurological disability in young and middle-aged adults. Typically, the disease becomes evident before the age of 30 in about 50% of patients; in 25% of the patients the onset of disease is between the ages of 30 to 40, and in 25% the disease appears between the ages of 40 to 50. The female to male ratio is 2:1(4).

MS and the resulting neurological damage have a major physical, psychological, social and financial impact on the patients and on their families. The most common clinical symptoms of MS are paresis, paraesthesia, visual impairment, sexual, bowel, and urinary dysfunction, spasticity, and incoordination. 40 to 50% of patients suffer from cognitive dysfunctions. The extent of neurological deficit, the rate of progression, and the frequency of relapses are highly variable among the affected individuals (2-3).

Most MS patients have a normal life span marked by numerous years of severe progressive disability. The causes of death in patients with MS are respiratory or urinary tract infections rather than the disease itself. There are several distinct types of MS: relapsing-remitting multiple sclerosis (RRMS), which is characterized by unpredictable acute episodes of neurological dysfunction (relapses), followed by variable recovery and periods of clinical stability. 80% to 85% of MS patients are diagnosed with RRMS. More than 50% of the patients having RRMS develop sustained deterioration with or without relapses superimposed; this form is called Secondary Progressive MS (SPMS). Some MS patients developing a progressive deterioration from the beginning can also develop relapses later on; this uncommon form is called primary progressive-relapsing multiple sclerosis (2-3).

Approximately 15% of overall MS patients develop a sustained deterioration of their neurological function from the beginning. This form is known as Primary Progressive MS or PPMS. The diagnosis is currently according to the McDonald's criteria (1). The outcome of a diagnostic evaluation is either "Multiple Sclerosis", "possible MS" (for those at risk for MS, but for whom diagnostic evaluation is equivocal), or "not MS" (1). Finally, the term clinically isolated syndrome (CIS) applies to those patients who have suffered a first clinical attack but do not comply with the classical diagnostic criteria for definite MS. Nowadays, the presence of new lesions in a second MRI performed at least three months apart is an accepted criterion for a diagnosis of MS in these patients. 10%-20% of patients with an isolated syndrome will not develop MS.

MS is an inflammatory disease that damages the myelin in the Central Nervous System (CNS) causing neurological impairment and, frequently, severe disability. The etiology of MS remains mostly unknown. It is generally assumed that MS is triggered by a combination of autoimmunity, infection and genetic predisposition (2-3). Autoimmune response against myelin components proceeding through the activation of CD4+ T lymphocytes, loss of proper regulation on Th1/Th2 lymphocytes, production of anti-myelin antibodies by B lymphocytes, and possibly, inhibition of CD8+ cytotoxic/suppressor lymphocytes underlie the pathogenesis of the MS.

MS is characterized by scattered regions of inflammation within the white substance of the CNS, brain and spinal cord. Focal inflammatory events eventually lead to demyelination of the axonal sheaths, degradation of nerve tissue, and finally, to irreversible neurological damage. Although the exact mechanism by which the MS process is initiated remains largely unknown, the target antigens of the autoimmune response in MS are believed to be part of the CNS myelin.

It is unclear whether the different courses of multiple sclerosis described are due to the same or to distinct pathophysiologic processes. Relapses are considered the clinical expression of acute inflammatory focal lesions whereas progression is considered to reflect the occurrence of demyelination, axonal loss and gliosis. Relapsing remitting multiple sclerosis and secondary progressive multiple sclerosis are probably different stages of the same disease while primary progressive multiple sclerosis may imply different processes.

Myelin basic protein (MBP) and proteolipid protein (PLP) are the most common myelin components. Additional, less abundant constituents of myelin, such as myelin associated glycoproteins (MAG), myelin oligodendrocyte glycoproteins (MOG), and α-B crystalline are also known. There is a considerable on-going debate regarding the true nature of the target antigen(s) in multiple sclerosis. In general, it appears that involvement of different antigens leads to certain differences in the courses of the disease (5-12).

MRI-Based Multiple Sclerosis Diagnostic Criteria

All the diagnostic criteria for establishing the diagnosis of MS proposed in the last 50 years are based on three main principles: (1) demonstration of demyelinating lesions disseminated in space (DIS); (2) demonstration of demyelinating lesions disseminated in time (DIT); and (3) reasonable exclusion of alternative explanations for the clinical presentation (13).

Conventional MRI

Conventional MRI techniques (cMRI), such as T2-weighted sequences and gadolinium-enhanced T1-weighted sequences, are highly sensitive for detecting MS plaques and can provide quantitative assessment of inflammatory activity and lesion load.

MRI studies in patients with Relapsing Remitting Multiple Sclerosis (RRMS) and Secondary Progressive Multiple Sclerosis (SPMS), using gadolinium diethylenetriamine pentaacetic acid (Gd-DTPA) as a contrast agent, indicating blood-brain barrier disruption, have revealed that disease activity (defined as the presence of Gd-enhancing lesions on T1-weighted MRI) is 5 to 10 times more frequent than is apparent from clinical criteria alone (14).

Non-Conventional MRI

Unenhanced T1-weighted imaging, measures of central nervous system atrophy, magnetization transfer imaging, proton magnetic resonance spectroscopy, diffusion-weighted imaging, and functional magnetic resonance imaging, provide a better approximation of the pathological substrate of the multiple sclerosis plaques, have increased the understanding of the pathogenesis of the disease, and have proven useful for studying the natural history of multiple sclerosis and monitoring the effects of new treatments (13).

Current Therapeutic Approaches

The vast majority of treatments for multiple sclerosis have either immunosuppressive or immunomodulatory nature.

Corticosteroids:

Corticosteroids shorten the duration of a relapse but do not generally affect the degree of recovery. They have unspecific immunomodulatory and anti-inflammatory effects that decrease the blood-brain barrier (BBB) permeability, reduce edema, and improve axonal conduction. Corticosteroids are often used to treat clinically significant relapses for a faster recovery. They have an acute anti-inflammatory activity which is short term and does not have an effect on the long term disease course.

Interferon Beta:

Two forms of recombinant interferon beta, beta-1a and beta-1b, have been approved for the treatment of patients with RRMS. The mechanism of their action in MS includes antiproliferative effects on T lymphocytes; decreased expression of major histocompatibility complex (MHC) class II antigens, and other immunoregulatory properties. The interferon-beta reduces the relapse rate in about 30% of patients with RRMS with mild to moderate disability. Major reduction in Gd-enhancing lesions on MRI scans could be demonstrated with interferon beta-1b, as well as reduction of EDSS progression. Interferon beta is administered as subcutaneous (s.c.) or intramuscular (i.m.) injection once or three times per week, depending on its type. It is associated with various adverse events, including flu-like symptoms, injection site reactions, serum aminotransferase elevation, and depression. Neutralizing antibodies have been reported in 5% to 40% of patients treated for three years and may lead to decreased efficacy.

Glatiramer Acetate:

Glatiramer acetate is a complex of synthetic peptides resembling myelin basic protein, which has shown a reduced annual rate of relapses of 30% in patients with RRMS. Glatiramer acetate is given daily by s.c. injection. The most common side effect is injection site reaction, which has been reported in up to 90% of patients. Another uncommon adverse event is a complex of immediate post injection reactions (IPIRs) which includes flushing, chest tightness, shortness of breath, palpitations, and anxiety.

Natalizumab:

Natalizumab is a humanized monoclonal antibody against the cellular adhesion molecule α4-integrin. Natalizumab is used in the treatment of multiple sclerosis and Crohn's disease. It is co-marketed by Biogen Idec and Élan as Tysabri, and was previously named Antegren. Natalizumab is administered by intravenous infusion every 28 days. The drug is believed to work by reducing the ability of inflammatory immune cells to attach to and pass through the cell layers lining the intestines and blood-brain barrier. Natalizumab has proven effective in treating the symptoms of both diseases, preventing relapse, vision loss, cognitive decline and significantly improving quality of life in people with multiple sclerosis, as well as increasing rates of remission and preventing relapse in Crohn's disease. Natalizumab was approved in 2004 by the United States Food and Drug Administration. It was subsequently withdrawn from the market by its manufacturer after it was linked with three cases of the rare neurological condition progressive multifocal leukoencephalopathy (PML) when administered in combination with interferon beta-1a, another immunosuppressive drug often used in the treatment of multiple sclerosis. After a review of safety information and no further deaths, the drug was returned to the US market in 2006 under a special prescription program. In the European Union, it has been approved only for the treatment of multiple sclerosis.

Antisense Theory

Antisense Oligonucleotides (AS-ONs) are short stretches of nucleotides or nucleotide derivatives that are complementary to a region of targeted RNA and can specifically suppress expression and other aspects such as processing of that particular transcript. The exact mechanism(s) of AS-ON action remains unclear, but is known to be different depending on the type of AS-ONs. Generally, these molecules block gene expression by hybridizing to the target mRNA, resulting in subsequent double-helix formation. This process can occur at any point such as transcription, initiation of translation, or during translation. Some of the possible mechanisms are disruption of splicing, impaired mRNA transport, disruption of translation of the transcripts as well as decreased stability of the mRNA transcript. In the case of many antisense oligodeoxyribonucleotides (AS-ODNs), cellular RNase H is able to bind to the DNA-RNA duplex and hydrolyze the RNA, resulting in reduced transcript numbers and decreased production of protein. Modifications to the deoxy moiety at the 2'-sugar position usually prohibits RNase H recruitment and action in that region of an AS-ODN (16).

Modified AS-ONs or AS-ON analogs are often employed for in vivo antisense applications due to their increased stability and nuclease resistance. A longer serum half-life ensures that the AS-ON has ample time to reach and interact with its target RNA in the tissue. AS-ODNs with phosphorothioate backbones are widely used due to their longer serum half-life and the fact that they are a suitable RNase H substrate. However, phosphorothioates display high affinity for various cellular proteins, which can result in sequence-nonspecific effects. Many AS-ONs with 2'-modifications of the sugar with groups such as O-methyl, fluoro, O-propyl, O-allyl, or many others exhibit greater duplex stability with their target mRNA and greater specificity but antisense effects in that 2' modified region are usually independent of RNase H. These modifications create bulk at the 2' position, causing steric hindrance to play a significant role in increasing nuclease resistance. Nucleotide analogs, such as peptide nucleic acids, generally are also nuclease-resistant and often demonstrate superior hybridization properties due to modified backbone charge, although they usually are not acceptable substrates for RNase H (16).

The traditional goal of the antisense approach to therapeutics is to decrease the level of key proteins in the disease pathogenesis. The use of antisense oligonucleotides as therapeutics has the potential advantage of much greater specificity compared to conventional small molecule drugs. The majority of drugs currently in use modulate the activity of specific proteins by either binding directly to the protein of interest or by binding to other proteins, such as cell surface receptors, which then modulate the target protein. Due to the large number of related proteins, activity classes and protein families performing the same or very similar function, small molecule drugs often bind to, and affect the activity of, more than one target protein. In contrast, the effectiveness of AS-ONs relies on highly specific base-pairing between the oligonucleotide and the target RNA. Therefore, antisense technology enables targeting of a single member of a closely-related protein family and designing therapeutic agents displaying fewer non-specific toxic effects than other, less selective, agents (17-21).

VLA-4 Integrin

Integrins are heterodimeric adhesion molecules that play key roles in leukocyte activation, trafficking, and signaling. The VLA-4 integrin consists of α4 chain non-covalently linked to the β1 subunit. It is expressed on most leukocytes, whether they occur in peripheral blood, lymphoid tissue, or at sites of inflammation in various organs. α4β1 binds to VCAM-1 on the activated endothelium and to the CS1 segment of fibronectin found in extracellular matrix. These interactions are critical for leukocyte migration across endothelium and into inflamed tissues. Ligand binding by α4 integrins has diverse biological consequences. The best-known role for α4 is its function as an adhesion molecule guiding leukocytes across vascular endothelium and into sites of inflammation. Leukocytes are recruited from the blood and into tissues by a multi-step process that involves an initial transient rolling of cells along the vascular endothelium followed by firm adhesion and subsequent trans-endothelial migration. The α4 integrin is unique among adhesion molecules in that it can support both the rolling and firm adhesion steps (22).

SUMMARY OF THE INVENTION

This invention provides a method for treating a human subject afflicted with a form of multiple sclerosis, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein
each of the 19 internucleotide linkages of the oligonucleotide is an O,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}$C),
or a pharmaceutically acceptable salt of the oligonucleotide,
so as to thereby treat the human subject.

This invention also provides a method for inhibiting the accumulation of new active brain lesions in a human subject afflicted with a form of multiple sclerosis detectable by MRI, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO: 1)

wherein
each of the 19 internucleotide linkages of the oligonucleotide is an O,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}$C),
or a pharmaceutically acceptable salt of the oligonucleotide,
so as to thereby inhibit the accumulation of new active brain lesions in the human subject detectable by MRI.

This invention additionally provides a method for inhibiting an increase in the volume of gadolinium-enhancing brain lesions of a human subject afflicted with a form of multiple sclerosis detectable by MRI, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein
each of the 19 internucleotide linkages of the oligonucleotide is an O,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}$C),
or a pharmaceutically acceptable salt of the oligonucleotide,
so as to thereby inhibit an increase in the volume of gadolinium-enhancing brain lesions detectable by MRI image.

This invention further provides a method for reducing level of VLA-4 in the blood of a human subject afflicted with a form of multiple sclerosis comprising periodically administering to the human subject a pharmaceutical composition comprising a pharmaceutically acceptable carrier and a therapeutically effective amount of an oligonucleotide having the structure:

5'-$^{Me}C^{Me}$UG AST $^{Me}$CTG TTT $^{Me}U^{Me}C^{Me}$C A$^{Me}U^{Me}$U $^{Me}C^{Me}$U-3' (SEQ ID NO:1)

wherein
each of the 19 internucleotide linkages of the oligonucleotide is an O,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines
or a pharmaceutically acceptable salt of the oligonucleotide,
so as to thereby reduce the level of VLA-4 in the blood of the human subject afflicted with the form of multiple sclerosis.

This invention also provides a method for inhibiting progression of disability in a human subject afflicted with a form of multiple sclerosis, comprising periodically administering to a human subject afflicted with multiple sclerosis a pharmaceutical composition comprising a pharmaceutically acceptable carrier and therapeutically effective amount of an oligonucleotide having the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO:1) wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;

the nucleotides at the positions 4 to 12 from the 5' end are 2'-deoxyribonucleosides;

the nucleotides at the positions 13 to 20 from the 5' end are 2'-O-(2-methoxyethyl) modified ribonucleosides; and all cytosines are 5-methylcytosines ($^{Me}$C), or a pharmaceutically acceptable salt of the oligonucleotide, so as to thereby inhibit progression of disability in the human subject.

This invention furthermore provides a method for reducing the relapse rate in a human subject afflicted with a relapsing form of multiple sclerosis, comprising periodically administering to the human subject a pharmaceutical composition comprising a pharmaceutically acceptable carrier and a therapeutically effective amount of an oligonucleotide having the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;

the nucleotides at the positions 4 to 12 from the 5' end are 2'-deoxyribonucleosides;

the nucleotides at the positions 13 to 20 from the 5' end are 2'-O-(2-methoxyethyl) modified ribonucleosides; and all cytosines ($^{Me}$C) are 5-methylcytosines, or a pharmaceutically acceptable salt of the oligonucleotide, so as to thereby reduce the relapse rate in the human subject afflicted with the relapsing form of multiple sclerosis.

This invention provides a method for inhibiting the accumulation of new active brain lesions, decreasing or inhibiting an increase in the volume of gadolinium-enhancing brain lesions, and reducing the relapse rate in a human subject afflicted with a relapsing form of multiple sclerosis, comprising periodically administering to the human subject a pharmaceutical composition comprising a pharmaceutically acceptable carrier and a therapeutically effective amount of an oligonucleotide having the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO:1)

wherein a) each of the 19 internucleotide linkages of the oligonucleotide is an O,O-linked phosphorothioate diester;

b) the nucleotides at the positions 1 to 3 from the 5' end are 2'-O-(2-methoxyethyl) modified ribonucleosides;

c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and e) all cytosines ($^{Me}$C) are 5-methylcytosines, or a pharmaceutically acceptable salt of the oligonucleotide, so as to thereby inhibit the accumulation of new active brain lesions, decrease or inhibit an increase in the volume of gadolinium-enhancing brain lesions and reduce the relapse rate in a human subject afflicted with the relapsing form of multiple sclerosis.

DETAILED DESCRIPTION OF THE INVENTION

Figure 1:
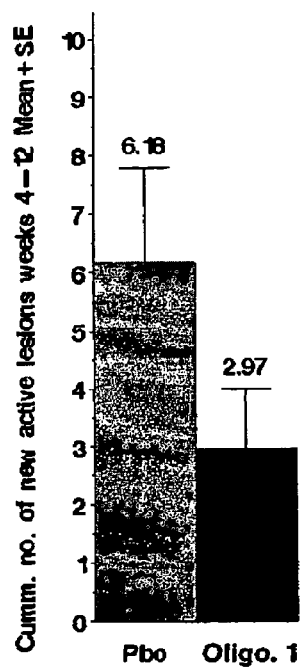
FIG. 1: (A, B and C) Illustrates the cumulative number of new active lesions measured by the MRI in the brain of RRMS patients on weeks 4, 8 and 12, treated with OLIGONUCLEOTIDE 1 compared to placebo. (C) OLIGONUCLEOTIDE 1 reduces the number of active lesions by 54.4%, p=0.01.
Figure 1:
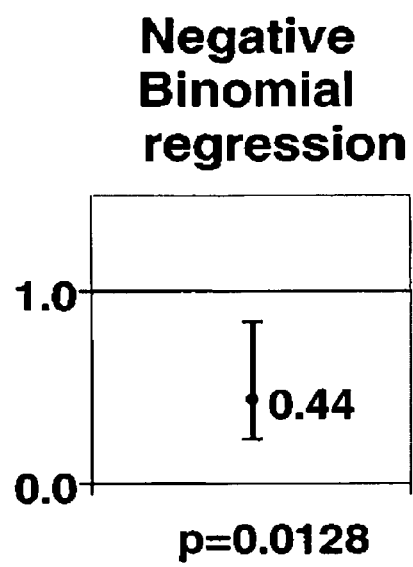
Figure 1:
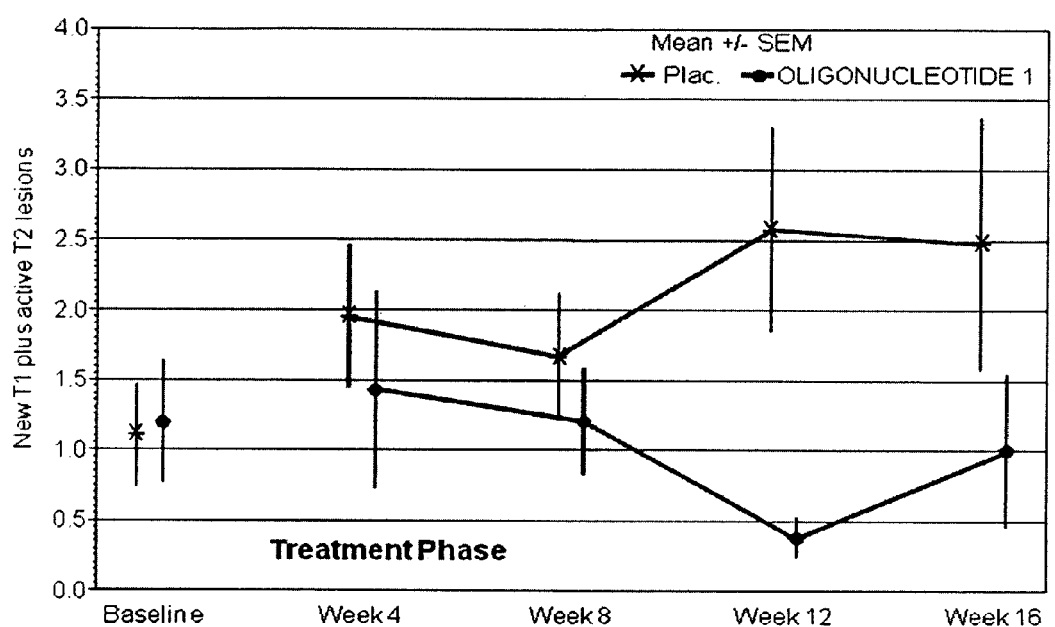

This invention provides a method for treating a human subject afflicted with a form of multiple sclerosis, comprising periodically administering to the human subject a pharmaceutical composition comprising a pharmaceutically acceptable carrier and a therapeutically effective amount of an oligonucleotide having the structure:

5'-$^{Me}$C$^{Me}$UG AGT $^{Me}$CTG TTT $^{Me}$U$^{Me}$C$^{Me}$C $^{Me}$A$^{Me}$U $^{Me}$U $^{Me}$C$^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;

the nucleotides at the positions 4 to 12 from the 5' end are 2'-deoxyribonucleosides;

the nucleotides at the positions 13 to 20 from the 5' end are 2'-O-(2-methoxyethyl) modified ribonucleosides; and all cytosines are 5-methylcytosines ($^{Me}$C), or a pharmaceutically acceptable salt of the oligonucleotide, so as to thereby treat the human subject.

In an embodiment of the method, the administration inhibits progression of disability in the human subject.

In another embodiment of the method, the progression of disability is reduced by 15%-70% as measured by EDSS score relative to the progression of disability in human subjects afflicted with the form of multiple sclerosis not so treated.

In an embodiment of the method, the administration inhibits the accumulation of new active brain lesions in the human subject detectable by MRI.

In an embodiment of the method, the number of new active brain lesions detectable by MRI is lower by 25%-80% than the number of new active brain lesions detectable by MRI in a human subject afflicted with the form of multiple sclerosis not treated with the pharmaceutical composition.

In an embodiment of the method, the number of new active brain lesions detectable by MRI is lower by 50%-65% after 8 weeks of treatment than the number of new active brain lesions detectable by MRI in a human subject afflicted with multiple sclerosis not so treated with the pharmaceutical composition. In an embodiment of the method, the periodic administration is three times per week.

In one embodiment, the administration inhibits an increase in the volume of gadolinium-enhancing brain lesions of the human subject detectable by MRI.

In a further embodiment, the administration results in a decrease in the volume of gadolinium-enhancing brain lesions of the human subject detectable by MRI.

In another embodiment, the volume of gadolinium-enhancing brain lesions of the human subject afflicted with the form of multiple sclerosis is 25%-80% less than the volume of gadolinium-enhancing brain lesions of a human subject afflicted with the form of multiple sclerosis not treated with the pharmaceutical composition, wherein the lesions are detectable by MRI.

In a further embodiment, the MRI method is selected from the group consisting of T2-weighted scanning, precontrast T1-weighted scanning, and post-gadolinium T1-weighted scanning.

In one embodiment, the periodic administration is twice per week.

In another embodiment, the periodic administration is once per week.

In a further embodiment, the periodic administration is once every two weeks.

In an additional embodiment, the periodic administration is once every three weeks.

In another embodiment, the periodic administration is once every four weeks.

In yet another embodiment, the periodic administration is once per month.

In a further embodiment, the periodic administration is once per two months.

In one embodiment of this invention, the therapeutically effective amount is 200, 400, 600, 800, 1000, 1200, 1400 or 1600 mg.

In an embodiment of the method, the amount effective to treat the human subject is 50-400 mg.

In an additional embodiment, the amount effective to treat the human subject is 200 mg.

In an embodiment of the method for periodic administration once per week, the amount effective to treat the human subject is 200 mg.

In an embodiment of the method for periodic administration once every two weeks, the amount effective to treat the human subject is 200 mg.

In an embodiment of the method for periodic administration once every four weeks, the amount effective to treat the human subject is 400 mg.

In an embodiment of the method, the average platelet count of the human subject is above 50,000 platelets per microliter of blood during the course of administration.

In an embodiment of the method, the average platelet count of the human subject is above 100,000 platelets per microliter of blood during the course of administration.

In an embodiment of the method, the average platelet count of the human subject is above 150,000 platelets per microliter of blood during the course of administration.

In a further embodiment of the method, the administration is effective to provide a $C_x$ of the oligonucleotide in the plasma of the human subject of 10,000-11,000 ng/ml.

In one embodiment of the method, the pharmaceutical composition is administered subcutaneously.

In another embodiment, the oligonucleotide is in the form of a sodium salt.

In an additional embodiment, the oligonucleotide is in the form of a potassium salt.

In yet another embodiment, the pharmaceutical carrier is WFI (water for injection) and the pharmaceutical composition is adjusted to pH 7.2-7.6. In a further embodiment, the pharmaceutical carrier is WFI (water for injection) and the pharmaceutical composition is adjusted to pH 7.4.

In an embodiment of the method, the form of multiple sclerosis is a relapsing form of multiple sclerosis.

In an additional embodiment, the form of multiple sclerosis is relapsing remitting multiple sclerosis.

In a further embodiment, the form of multiple sclerosis includes, and OLIGONUCLEOTIDE 1 treats, at least one of the following symptoms: the accumulation of new active brain lesions, the increase in volume of gadolinium-enhanced lesions, progressive disability, an increase in the relapse rate, optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

In another embodiment, the administration reduces relapse rate in the human subject.

This invention furthermore provides a method for reducing the relapse rate in a human subject afflicted with a relapsing form of multiple sclerosis, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines ($^{Me}C$) are 5-methylcytosines,
or a pharmaceutically acceptable salt of the oligonucleotide,
so as to thereby reduce the relapse rate in the human subject afflicted with the relapsing form of multiple sclerosis.

This invention furthermore provides a method for inhibiting the accumulation of new active brain lesions, decreasing or inhibiting an increase in the volume of gadolinium-enhancing brain lesions, and reducing the relapse rate in a human subject afflicted with a relapsing form of multiple sclerosis, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}$U$^{Me}$C$^{Me}$C A$^{Me}$U$^{Me}$U $^{Me}C^{Me}$U-3' (SEQ ID NO:1)

wherein
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the end are 2'-O-(2-methoxyethyl) modified ribonucleosides; and
e) all cytosines ($^{Me}C$) are 5-methylcytosines,
or a pharmaceutically acceptable salt of the oligonucleotide,
so as to thereby inhibit the accumulation of new active brain lesions, decrease or inhibit an increase in the volume of gadolinium-enhancing brain lesions and reduce the relapse rate in a human subject afflicted with the relapsing form of multiple sclerosis In another embodiment of the method, the method further comprises inhibiting progression of disability in the human subject In another embodiment of the method, the progression of disability is reduced by 15%-70% as measured by EDSS score relative to the progression of disability in human subjects afflicted with the form of multiple sclerosis not so treated.

In an embodiment of the method, the relapsing form of multiple sclerosis is relapsing remitting multiple sclerosis.

In another embodiment, the relapse rate is reduced by more than 30% relative to the relapse rate of patients not so treated.

In an embodiment of the method, the number of new active brain lesions detectable by MRI is lower by 25%-80% than the number of new active brain lesions detectable by MRI in a human subject afflicted with the form of multiple sclerosis not treated with the pharmaceutical composition.

In an embodiment of the method, the number of new active brain lesions detectable by MRI is lower by 50%-65% after 8 weeks of treatment than the number of new active brain lesions detectable by MRI in a human subject afflicted with multiple sclerosis not so treated with the pharmaceutical composition.

In another embodiment, the volume of gadolinium-enhancing brain lesions of the human subject afflicted with the form of multiple sclerosis is 25%-80% less than the volume of gadolinium-enhancing brain lesions of a human subject afflicted with the form of multiple sclerosis not treated with the pharmaceutical composition, wherein the lesions are detectable by MRI.

In a further embodiment, the MRI method is selected from the group consisting of T2-weighted scanning, precontrast T1-weighted scanning, and post-gadolinium T1-weighted scanning.

In one embodiment, the periodic administration is twice per week.

In another embodiment, the periodic administration is once per week.

In a further embodiment, the periodic administration is once every two weeks.

In an additional embodiment, the periodic administration is once every three weeks.

In another embodiment, the periodic administration is once every four weeks.

In yet another embodiment, the periodic administration is once per month.

In a further embodiment, the periodic administration is once per two months.

In one embodiment of this invention, the therapeutically effective amount is 200, 400, 600, 800, 1000, 1200, 1400 or 1600 mg.

In an embodiment of this invention, the amount effective to treat the human subject is 50-400 mg.

In an additional embodiment, the amount effective to treat the human subject is 200 mg.

In an embodiment of the method for periodic administration once per week, the amount effective to treat the human subject is 200 mg.

In an embodiment of the method for periodic administration once every two weeks, the amount effective to treat the human subject is 200 mg.

In an embodiment of the method for periodic administration once every four weeks, the amount effective to treat the human subject is 400 mg.

In an embodiment of the method, the average platelet count of the human subject is above 50,000 platelets per microliter of blood during the course of administration.

In an embodiment of the method, the average platelet count of the human subject is above 100,000 platelets per microliter of blood during the course of administration.

In an embodiment of the method, the average platelet count of the human subject is above 150,000 platelets per microliter of blood during the course of administration.

In a further embodiment of the method, the administration is effective to provide a $C_{max}$ of the oligonucleotide in the plasma of the human subject of 10,000-11,000 ng/ml.

In one embodiment of the method, the pharmaceutical composition is administered subcutaneously.

In another embodiment, the oligonucleotide is in the form of a sodium salt.

In an additional embodiment, the oligonucleotide is in the form of a potassium salt.

In yet another embodiment, the pharmaceutical carrier is WFI (water for injection) and the pharmaceutical composition is adjusted to pH 7.2-7.6. In a further embodiment, the pharmaceutical carrier is WFI (water for injection) and the pharmaceutical composition is adjusted to pH 7.4.

In another embodiment, the pharmaceutical composition is administered as a monotherapy.

In a further embodiment, the pharmaceutical composition is administered simultaneously or sequentially with at least one additional therapeutic agent.

In an embodiment, the additional therapeutic agent is a corticosteroid, interferon beta-1a, interferon beta-1b, glatiramer acetate or natalizumab.

In yet another embodiment, the additional therapeutic agent is a corticosteroid.

In a further embodiment, the additional therapeutic agent is glatiramer acetate.

This invention further provides a method for reducing level of VLA-4 in the blood of a human subject afflicted with a form of multiple sclerosis comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;

the nucleotides at the positions 4 to 12 from the 5' end are 2'-deoxyribonucleosides;

the nucleotides at the positions 13 to 20 from the 5' end are 2'-O-(2-methoxyethyl) modified ribonucleosides; and all cytosines are 5-methylcytosines ($^{Me}$C), or a pharmaceutically acceptable salt of the oligonucleotide, so as to thereby reduce the level of VLA-4 in the blood of the human subject afflicted with the form of multiple sclerosis.

In an embodiment of the method, the level of VLA-4 in the blood of the human subject is reduced by more than 15% relative to a human subject not so treated. In an additional embodiment the level of VLA-4 in the blood of the human subject is reduced by 10%-90% relative to a human subject not so treated. The level of VLA-4 reduction in these embodiments may be for example reduction of mRNA, protein or cell surface VLA-4. Furthermore, this level of reduction may be in one or a few of the leukocyte subsets in the blood.

In an embodiment of this invention, the periodic administration is three times per week.

In one embodiment, the periodic administration is twice per week.

In another embodiment, the periodic administration is once per week.

In a further embodiment, the periodic administration is once every two weeks.

In an additional embodiment, the periodic administration is once every three weeks.

In yet another embodiment, the periodic administration is once per month.

In a further embodiment, the periodic administration is once per two months.

In one embodiment of the method, the therapeutically effective amount is 200, 400, 600, 800, 1000, 1200, 1400 or 1600 mg.

In an embodiment of the method, the amount effective to treat the human subject is 50-400 mg.

In an additional embodiment, the amount effective to treat the human subject is 200 mg.

In an embodiment of the method for periodic administration once per week, the amount effective to treat the human subject is 200 mg.

In an embodiment of the method for periodic administration once every two weeks, the amount effective to treat the human subject is 200 mg.

In an embodiment of the method for periodic administration once every four weeks, the amount effective to treat the human subject is 400 mg.

In an embodiment of the method, the average platelet count of the human subject is above 50,000 platelets per microliter of blood during the course of administration.

In an embodiment of the method, the average platelet count of the human subject is above 100,000 platelets per microliter of blood during the course of administration.

In an embodiment of the method, the average platelet count of the human subject is above 150,000 platelets per microliter of blood during the course of administration.

In a further embodiment of the method, the administration is effective to provide a $C_{max}$ of the oligonucleotide in the plasma of the human subject of 10,000-11,000 ng/ml.

In one embodiment of the method, the pharmaceutical composition is administered subcutaneously.

In another embodiment, the oligonucleotide is in the form of a sodium salt.

In an additional embodiment, the oligonucleotide is in the form of a potassium salt.

In yet another embodiment, the pharmaceutical carrier is WFI (water for injection) and the pharmaceutical composition is adjusted to pH 7.2-7.6. In a further embodiment, the pharmaceutical carrier is WFI (water for injection) and the pharmaceutical composition is adjusted to pH 7.4.

This invention also provides a method for inhibiting the accumulation of new active brain lesions in a human subject afflicted with a form of multiple sclerosis detectable by MRI, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;

the nucleotides at the positions 4 to 12 from the 5' end are 2'-deoxyribonucleosides;

the nucleotides at the positions 13 to 20 from the 5' end are 2'-O-(2-methoxyethyl) modified ribonucleosides; and all cytosines are 5-methylcytosines ($^{Me}$C), or a pharmaceutically acceptable salt of the oligonucleotide, so as to thereby inhibit the accumulation of new active brain lesions in the human subject detectable by MRI.

This invention additionally provides a method for inhibiting an increase in the volume of gadolinium-enhancing brain lesions of a human subject afflicted with a form of multiple sclerosis detectable by MRI, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO:1)

wherein each of the 19 internucleotide linkages of the oligonucleotide is an O,O-linked phosphorothioate diester;

the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}C$),
or a pharmaceutically acceptable salt of the oligonucleotide,
so as to thereby inhibit an increase in the volume of gadolinium-enhancing brain lesions detectable by MRI image.

This invention also provides a method for inhibiting progression of disability in a human subject afflicted with a form of multiple sclerosis, comprising periodically administering to a human subject afflicted with multiple sclerosis a pharmaceutical composition comprising a pharmaceutically acceptable carrier and therapeutically effective amount of an oligonucleotide having the structure:

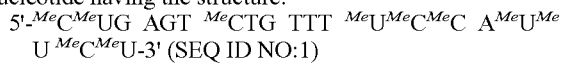

wherein
each of the 19 internucleotide linkages of the oligonucleotide is an O,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}C$),
or a pharmaceutically acceptable salt of the oligonucleotide,
so as to thereby inhibit progression of disability in the human subject.

As used herein, an "additional therapeutic agent" is any agent useful for treating multiple sclerosis other than OLIGONUCLEOTIDE 1.

Within any range listed in this document, all integers, and tenths, including integer percentages for percentages, are contemplated as embodiments of this invention. For example, the invention provides that the amount effective to treat the human subject may be 50-400 mg; by this recitation the invention contemplates and discloses all tenths and integer mg amounts such as 51.1, 51.2 . . . 399.8, 399.9; 51, 52 . . . 398, 399 mg as embodiments of this invention. Similarly, by another example, the invention provides that the number of new active brain lesions detectable by MRI image is lower by 25-80% than the number of new active brain lesions detectable by MRI image in a human subject afflicted with multiple sclerosis not treated with the pharmaceutical composition; by this recitation the invention contemplates and discloses all integer % amounts such as 26%, 27%, 28% . . . 78% and 79% as embodiments of this invention. Analogously for every range disclosed in this application.

A pharmaceutically acceptable salt as used herein refers to any salt form of the oligonucleotide 3-9-8 MOE gap-mer disclosed herein which is appropriate to administer to a human subject. In particular, a potassium salt or a sodium salt as exemplified herein can be used.

Definitions

Kurtzke Expanded Disability Status Scale (EDSS)

The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (ES) and allows neurologists to assign a Functional System Score (FSS) in each of these. The Functional Systems are: pyramidal, cerebellar, brainstem, sensory, bowel and bladder, visual & cerebral.

Multiple Sclerosis Functional Composite (MSFC):

Multiple Sclerosis Functional Composite (MSFC) is a three-part, standardized, quantitative, assessment instrument for use in clinical studies, particularly clinical trials, of MS (23). The MSFC was designed to fulfill three criteria: multi-dimensional to reflect the varied clinical expression of MS across patients and over time, the dimensions should change relatively independently over time, and one component should be a measure of cognitive function. The three components of the MSFC measure leg function/ambulation, arm/hand function, and cognitive function. MSFC measures disability in MS patients; and used in evaluating the efficacy of experimental or new treatment regimens. MSFC consists of various elements designed to measure arm, leg, and cognitive disability and includes a timed 25-foot walk to measure leg mobility, a nine-hole peg test to measure arm function, and a paced auditory serial addition test to measure cognitive function.

Image Contrast on MRI:

Time constants are involved in relaxation processes that establish equilibrium following radio frequency excitation. As the high-energy nuclei relax and realign they emit energy at rates which are recorded to provide information about the material they are in. The realignment of nuclear spins with the magnetic field is termed longitudinal relaxation and the time required for a certain percentage of the tissue's nuclei to realign is termed Time 1" or T1 (Spin-lattice relaxation time), which is typically about 1 second at 1.5 tesla main field strength. T2-weighted imaging relies upon local dephasing of spins following the application of the transverse energy pulse; the transverse relaxation time is termed Time 2" or T2 (spin-spin relaxation time), typically <100 ms for tissue at 1.5 tesla main field strength.

Image contrast is created by using a selection of image acquisition parameters that weights signal by T1 or T2. In the brain, T1-weighting causes the nerve connections of white matter to appear white, and the congregations of neurons of gray matter to appear gray, while cerebrospinal fluid appears dark. The contrast of "white matter," "gray matter'" and "cerebrospinal fluid" is reversed using T2 imaging.

As used herein, the term MRI refers to conventional or non-conventional MRI.

Gd-Enhancing Lesions:

The term "Gd-enhancing lesions" refers to lesions that result from a breakdown of the blood brain barrier, which appear in contrast studies using gadolinium contrast agents. Gadolinium enhancement provides information as to the age of a lesion, as Gd-enhancing lesions typically occur within a six week period of lesion formation.

T1-Weighted MRI Image:

The term "T1-weighted MRI image" refers to an MR-image that emphasizes T1 contrast by which lesions may be visualized. Abnormal areas in a T1-MRI weighted image are "hypointense" and appear as dark spots. These spots are generally older lesions.

T2-Weighted MRI Image:

The term "T2-weighted MRI image" refers to an MR-image that emphasizes T2 contrast by which lesions may be visualized. T2 lesions represent new inflammatory activity. T2 hyperintensity reflect a range of pathological changes from acute inflammation to irreversible axonal loss.

Relapses:

Relapses are characterized by the occurrence of neurological dysfunction symptoms, appearing after a 30-day period of stability or improvement and lasting for more than 24 hours (no infection, no fever). The number of relapses are analyzed using a logistic regression model controlling for treatment and age.

"Relapse Rate" is the number of confirmed relapses per unit time. "Annualized relapse rate" is the mean value of the number of confirmed relapses per each patient multiplied by 365 and divided by the number of days on study drug per each patient.

Progression of Disability:

Progression of disability is assessed by means of valid, sensitive and reliable scales such as EDSS and MSFC. Progression of disability is measured as the achievement of a specified degree of disability or of a sustained worsening of relevant magnitude (1 point when EDSS scores ≤5.5; 0.5 points if baseline score is >5.5). Alternatively, it can be measured as the time to reach progression or the proportion of individuals who have shown progression at pre-specified time. As a supportive parameter, disability can also be expressed by summary measures obtained from serial measures at scheduled visits, indicating the degree of disability experienced by the patient during a period of time, disregarding whether it is in relation to relapses or not.

OLIGONUCLEOTIDE 1:

OLIGONUCLEOTIDE 1 is a second generation phosphorothioate backbone 2'-MOE-modified chimeric oligonucleotide gap-mer designed to hybridize to the 3'-untranslated region of human Very Late Activation Antigen 4 mRNA (VLA-4 mRNA), also known as CD49d mRNA, which codes for the alpha-4 subunit of VLA-4. VLA-4 is also known as alpha-4 integrin (alpha4 beta1). OLIGONUCLEOTIDE 1 selectively inhibits VLA-4 expression in both primary human cells and in several human cell lines by hybridizing to mRNA encoding CD49, which is the α4 subunit of VLA-4.

OLIGONUCLEOTIDE 1 is the 19-sodium salt of a phosphorothioate oligonucleotide 20-mer also referred as a 3→9-8 MOE gap-mer having a molecular weight of 7230 Daltons, in which the nucleotides at positions 1 to 3 from the 5' end are 2'-O-(2-methoxyethyl) modified ribonucleosides (2'-O-(2-methoxyethyl ribose); the nucleotides at positions 4 to 12 from the 5' end are 2'-deoxyribonucleosides of which all cytosines are 5-methylcytosines; the nucleotides at positions 13 to 20 from the 5' end are 2'-O-(2-methoxyethyl) modified ribonucleosides.

The sequence of OLIGONUCLEOTIDE 1 (SEQ ID:1) is:

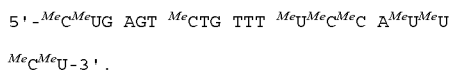

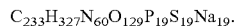

The empirical formula of OLIGONUCLEOTIDE 1 is:

$C_{233}H_{327}N_{60}O_{129}P_{19}S_{19}Na_{19}$.

OLIGONUCLEOTIDE 1 may be synthesized by a multistep process that may be divided into two distinct operations: solid-phase synthesis and downstream processing. In the first operation, the nucleotide sequence of OLIGONUCLEOTIDE 1 is assembled through a computer-controlled solid-phase synthesizer. Subsequent downstream processing includes deprotection steps, preparative reversed-phase (RP) chromatographic purification, isolation and drying to yield OLIGONUCLEOTIDE 1 drug substance. The chemical synthesis of OLIGONUCLEOTIDE 1 utilizes phosphoramidite coupling chemistry followed by oxidative sulfurization and involves sequential coupling of activated monomers to an elongating oligomer, the 3'-terminus of which is covalently attached to the solid support.

Detritylation (Reaction a)

Each cycle of the solid-phase synthesis commences with removal of the acid-labile 5'-O-4,4'-dimethoxytrityl (DMT) protecting group of the 5' terminal nucleoside of the support bound oligonucleotide. This is accomplished by treatment with an acid solution (for example dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g. for $B_2$: MOE-$^{Me}C$ amidite) in the presence of an activator (for example, 1H-tetrazole). This results in the formation of a phosphite triester linkage between the incoming nucleotide synthon and the support-bound oligonucleotide chain. After the coupling reaction excess reagent is removed from the support by washing with acetonitrile in preparation for the next reaction.

Sulfurization (Reaction c)

The newly formed phosphite triester linkage is converted to the corresponding (O,O,O)-trialkyl phosphorothioate triester by treatment with a solution of a sulfur transfer reagent (for example, phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ('DMT-on (n−1)-mers') which are difficult to separate from the desired product. To prevent formation of these impurities and to facilitate purification, a 'capping reagent' (for example acetic anhydride and N-methylimidazole/acetonitrile/pyridine) is introduced into the reactor vessel to give capped sequences. The resulting failure sequences ('DMT-off shortmers') are separated from the desired product by reversed phase HPLC purification. After the capping reaction excess reagent is removed from the support by washing with acetonitrile in preparation of the next reaction.

Reiteration of this basic four-step cycle using the appropriate protected nucleoside phosphoramidite allows assembly of the entire protected OLIGONUCLEOTIDE 1 sequence.

Backbone Deprotection (Reaction e)

Following completion of the assembly portion of the process the cyanoethyl groups protecting the (O,O,O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed-phase high pressure liquid chromatography (RP-HPLC). The RP-HPLC step removes DMT-off failure sequences. The elution profile is monitored by UV absorption spectroscopy. Fractions containing DMT-on OLIGONUCLEOTIDE 1 product are collected and analyzed.

Acidic Deprotection (Reaction g)

RP-HPLC fractions containing 5'-O-DMT-protected OLIGONUCLEOTIDE 1 are pooled and transferred to a precipitation tank. The products obtained from the purification of several syntheses are combined at this stage of the process. Purified DMT-on OLIGONUCLEOTIDE 1 is treated with acid (for example, acetic acid) to remove the DMT group attached to the 5'terminus. After acid exposure for the prescribed time and neutralization, OLIGONUCLEOTIDE 1 drug substance is isolated and dried.

Following the final acidic deprotection step (reaction g), the solution is neutralized by addition of aqueous sodium hydroxide and OLIGONUCLEOTIDE 1 drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 h. The temperature is increased to 30° C. and a secondary drying step performed for 5.5 h. Following completion of the lyophilization process, the drug substance is transferred to high density polyethylene bottles and stored at −20° C.

Forms of Multiple Sclerosis:

There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS; and
5) primary progressive multiple sclerosis (PPMS)

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS (5).

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process (24, 25).

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:

The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RRMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

As used herein, "course of administration" refers to the entire treatment from the first administration of the compound and continuing until any cessation of periodic administration. For example, the compound may be administered once every month for 2 months, or for 6 months, or for 12 months, or for 2 years, etc.

Thrombocytopenia

Human blood contains approximately 150,000 to 440,000 platelets per microliter. Bleeding can occur with relatively minor trauma when the platelet count falls below about 50,000 platelets per microliter of blood. Serious risks generally do not occur until the platelet count falls below 10,000 to 20,000 platelets per microliter, where bleeding may occur without any injury (26).

"$C_{max}$" refers to the maximum or "peak" concentration of a drug observed after its administration. $C_{min}$, refers to the minimum or "trough" concentration of a drug observed after its administration and just prior to the administration of a subsequent dose.

EXAMPLES

OLIGONUCLEOTIDE 1 can be obtained by the process disclosed in U.S. Pat. Nos. 5,968,826, 6,242,591 and 6,258,790, the contents of which are hereby incorporated by reference.

Example 1

To evaluate the efficacy and safety of a selected treatment regimen of OLIGONUCLEOTIDE 1 using MRI in patients with Relapsing Remitting MS (RRMS) compared to placebo.

A double-blind, placebo-controlled, multi-centre, randomized trial was conducted in order to prove the therapeutic concept and to determine the pharmacokinetic profile of OLIGONUCLEOTIDE 1 (VLA-4 antisense oligonucleotide) by subcutaneous injections, in 77 subjects diagnosed with RRMS (see Table I).

Methods

In order to be included in the study males and females of 18-55 years of age must have been diagnosed with Relapsing Remitting Multiple Sclerosis (RRMS).

Patients must have at least 9 T2 lesions or at least 4 if one is gadolinium-enhancing;

patients must have had at least one relapse within the last 12 months;

patients must have had no relapse four weeks prior to the beginning of the study;

patients must have EDSS score of 0-6.0;

patients must be able to provide written informed consent; and patients of childbirth potential must use reliable contraception such as surgical sterilization, oral contraceptives.

Exclusion Criteria were as Follows:

Use of any investigational drug within two months prior to the enrolment or within four months if the investigational drug is a new chemical entity;

patients with progressive disease;

patients having concomitant clinically relevant findings on MRI that may interfere with outcome assessment;

patients who have had been treated with VLA-4 antibodies, anti-CD4 antibodies, or other monoclonal antibodies;

patients who have underwent total lymphoid irradiation at any time;

patients who have received immune-modulating drugs within two months or immune-suppressive drugs within six months prior to the enrolment;

patients who are HIV positive;

patients having detectable levels of JC Virus in the blood measured by Quantitative PCR;

patients with renal impairment having serum creatinine 2.0 mg/dl;

patients having a history of clinically relevant gastrointestinal, hepatic, renal, endocrine, hematological, metabolic, neurologic (other than MS) or psychiatric disease;

patients with infections having lymphocyte count of >3000/μL;

patients having a history of any bleedings;

patients having a history of coagulation abnormalities;

patients who receive concomitant acetyl salicylic acid (>300 mg/day) and phenprocoumon;

female patients who are pregnant or breast feeding;

patients having a history of drug or alcohol abuse;

patients having clinically relevant abnormalities in physical findings at screening examination if interfering with the study objective; Patients who have epilepsy;

suicidal subjects;

patients having a history of drug allergy and/or known drug hypersensitivity; patients who are unable to communicate or to cooperate with the Investigator due to language problem;

patients having poor mental development or impaired cerebral function;

patients having any medical condition which, in the judgment of the Investigator, might interfere with the objectives of the study;

patients who have repeated participation in the study;

patients who have contraindication for application of the study drug;

patients who have been treated with corticosteroid within six weeks prior to the enrolment and during the study period; and patients must not have MRI exclusion criteria such as metal residing in the body (e.g. implants), cardiac pacemaker, valves, cochlear implants, CNS vascular clips, contrast medium allergy (Gd-DTPA).

TABLE I

Patient Populations
Number of patients in analysis populations per treatment group

| | Placebo | OLIGONUCLEOTIDE 1 | Total |
|---|---|---|---|
| Patients Randomized | 41 (100%) | 36 (100%) | 77 (100%) |
| Safety Population (randomized and treated) | 41 (100%) | 36 (100%) | 77 (100%) |
| ITT Population (valid MRI at screening at least one post-baseline MRI) | 39 (95.1%) | 35 (97.2%) | 74 (96.1%) |

TABLE II

Patient Baseline Characteristics

| Baseline Characteristic | Statistic | Placebo N = 41 | OLIGONUCLEOTIDE 1 N = 36 |
|---|---|---|---|
| Age (years) | Mean (SD) | 38.0 (9.90) | 39.6 (8.78) |
| Gender: Female | n (%) | 25 (61.0) | 26 (72.2) |
| Male | n (%) | 16 (39.0) | 10 (27.8) |
| Duration of MS (years) | Mean (SD) | 3.76 (4.14) | 5.67 (6.48) |
| EDSS score | Mean (SD) | 2.83 (1.42) | 2.49 (1.17) |
| T1 lesion | Mean (SD) | 1.1 (2.28) | 1.2 (2.58) |
| T1 lesion volume (mm$^3$) | Mean (SD) | 121 (305.7) | 151 (370.6) |

OLIGONUCLEOTIDE 1 Administration 36 eligible patients received OLIGONUCLEOTIDE 1 in the following manner:

I. Induction Cycle:

the patients were administered with three subcutaneous 'induction' doses of OLIGONUCLEOTIDE 1 200 mg/injection each, on days 1, 4, and 7.

II. Maintenance Cycle:

followed the induction cycle and comprised subcutaneous administration of 200 mg/injection of OLIGONUCLEOTIDE 1 twice a week (on days 4 and 7 of the week); lasted seven weeks.

III. Off-Treatment Cycle:

followed the maintenance cycle; lasted eight weeks.

41 eligible patients received placebo, in a similar manner as OLIGONUCLEOTIDE 1. 77 patients had completed the study.

OLIGONUCLEOTIDE 1 Product

The subcutaneous solution for injection contained only OLIGONUCLEOTIDE 1, in WFI (water for injection) adjusted to pH 7.4 with acid or base during compounding. The solution was clear with a light yellow color. It was packaged in Type I, flint glass vial that was stoppered with a bromobutyl rubber closure having a Teflon° coating and sealed with an aluminum flip-off overseal.

The eligible patients were randomly assigned to one of the following treatment groups:

Treatment Group A:

| Active treatment (OLIGONUCLEOTIDE 1) | Total Dose Applied |
|---|---|
| Subcutaneous injection containing OLIGONUCLEOTIDE 1 | 3400 mg |

Treatment Group B:

| Placebo treatment (Placebo) | Total Dose Applied |
|---|---|
| Subcutaneous injection containing sodium chloride and colorant only | none |

Each patient received a patient pack which consisted of 34 vials (+2 reserve vials) containing 100 mg OLIGONUCLEOTIDE 1 or 34 vials (+2 reserve vials) containing placebo solution each, and 36 syringes suitable for subcutaneous injection. A tear-off label was attached to the patient pack.

Baseline MRI was performed on Day −7 of the study;
week 4 MRI was performed following the 9th dose;
week 8 MRI was performed following the 17th dose; and
the Kurtzke Expanded-Disability-Status-Scale (EDSS) assessments were performed at visits 1, 5, 6, and 8 and also when a relapse occurred.

Measurements

Vital Signs:

Vital signs were measured at visits 1 and 6. After the patient had been supine for 5 minutes, the systolic and diastolic blood pressure and pulse rate were measured in the supine position and always on the same arm of the patient.

Electrocardiogram (ECG):

A 12-lead ECG was performed at visits 1 and 6 after the patient had been supine for 5 minutes.

Blood Samples:

Blood samples for hematology, clinical chemistry and coagulation parameters were collected from each patient for determination of the following parameters at visit 1 and at visits 5, 6, and 8. Analysis of blood samples were carried out at local certified laboratories. Complement fragment Bb were analyzed at Bioscientia in Ingelheim.

Hematology:
Erythrocytes, leucocytes, neutrophils, platelets, hematocrit, hemoglobin, WBC (total), lymphocytes, monocytes.

Clinical Chemistry:
Sodium, potassium, urea, alkaline phosphatase, glucose, γ-GT, SGOT, SGPT, total bilirubin, total protein, creatinine.

Coagulation Parameters:
Partial thromboplastine time, PT, TT.

Blood Samples for CD8+/CD4+ Cells:
Were collected at visits 2, 6, 7 and 8. CD8+/CD4+ cell assays was carried out at the University Essen.

Blood Samples for JC Virus Monitoring:
Were collected at visits 1, 5, 6, 7, and 8. JC virus monitoring by qPCR analysis of plasma was performed on an on-going basis and buffy coat cells had been stored frozen for possible analysis at the end of trial. The assay was carried out by Bioscientia, Ingelheim.

Blood Samples for HIV Screen:
Were collected at visit 1. HIV screening was carried out by Bioscientia, Ingelheim.

Urine Samples:
Urine samples for JC virus monitoring were collected from each patient at visits 1, 5, 6, 7, and 8. JC virus monitoring assay was carried out by Bioscientia, Ingelheim. Urinanalysis was performed at the local laboratory.

MRI:
Five MRI scans were performed per patient, to be taken for baseline setting (Day −7), at week 4 (after 9 doses), week 8 (after 17 doses), week 12, and week 16. An additional MRI scan was performed in case of relapse. MRI assessment was done by:
T2-weighted images;
Precontrast T1-weighted images; and
Post-gadolinium T1-weighted images.

MRI scans were analyzed by the IAC (Image Analysis Centre, VU Medical Centre, Amsterdam, The Netherlands) by an experienced reader blinded to treatment allocation.

Prior to initiation, each centre had asked to send a dummy scan to assess image quality and shipment procedures, and to evaluate the accessibility of the electronic data carrier. This was used to fine-tune the exact MRI sequences, which were vendor-specific. Only upon final approval of the dummy scan were the sites allowed to start scanning patients, with no deviations from the final scan-protocol for that particular site being allowed. Once patients had been enrolled, for each scan performed, the quality was assessed at the IAC and was reported to the contributing site, as part of an ongoing Quality Assurance procedure. Once the data had arrived at the IAC they were logged, copied and stored. Both sites and monitors were duly informed by fax about acceptance of scans. Lesions were marked on the hard copies by a radiologist blinded to full patient identification and treatment allocation.

MRI Image Acquisition:

The patient's position had been standardized by putting the patient's head into the head-coil in a well-defined fashion (e.g. nasal bridge at the centre). Rotation in the coronal plane was minimized by centering a horizontal light beam at the centre of the coil as well as across the orbital ridge. The head of the patient had been supported within the head-coil with foam cushions in order to minimize patient motion. Rotation in the horizontal plane had been minimized by centering a vertical light beam on the nose. A long IV line connected to a drip infusion with saline had been inserted prior to moving the patient into the scanner so that gadolinium could be injected during the session without moving the table (thus avoiding movement of the patients head between sequences).

All MR sequences were performed using 3 mm thick slices, with a 25 cm field of view (FOV), and a 256×256 square matrix to produce roughly 1 by 1 mm pixels. The actual scanning started with sagittal T1-weighted spin-echo (SE) localizer images. All transaxial images were planned from the mid-sagittal image, using 2×23 interleaved sections with a thickness of 3 mm using a 3 mm (100%) gap. This resulted in 46 consecutive slices with a Z-range of 13.8 cm, thus covering the head from vertex to foramen magnum; the middle slice of the upper series was aligned with the inferior border of the splenium of the corpus callosum.

A rectangular (e.g. ¾ or 75%) FOV was used. It allowed a proportional reduction in the number of phase encoding steps (e.g. 192 instead of 256), as long as 1×1 mm square pixels were obtained without unfolding artifacts (right to left phase encoding for the transaxial images). Techniques such as "half-Fourier transform", "reduced scan-percentage" (Philips Healthcare; Best, The Netherlands) or "1/2 NEX" (General Electric Healthcare; Tirat Hacarmel, Israel) were not employed, as they substantially reduce the signal-to-noise ratio.

The first transaxial sequence (following the pilot scans), was a pre-contrast T1-weighted conventional spin-echo (SE) [TR 400-700 ms/TE 5-25 ms/2 excitations]. Afterwards, gadolinium-DTPA was administered at a standard dose of 0.1 mmol/kg, via the long IV line. The second transaxial series was a dual echo SE [2000-3000 ms/TE1: 15-40 ms, TE2: 60-100 ms/1 excitation]. When a turbo- or fast-SE was used the turbo-factor was limited (e.g. 5-6). The third and final transaxial sequence was a poet-contrast T1-weighted conventional SE [400-700 ms/5-25 ms/2 excitations].

Pharmacokinetics:
  Oligonucleotide 1:
    Blood samples (7 ml) were obtained on visits 2, 5, 6, and 8 for evaluating oligonucleotide 1 plasma levels. On visits 2, 5, and 6 this was performed prior to and 1, 2, 3, 4, and 6 hours after injection of OLIGONUCLEOTIDE 1/Placebo. On visit 8 a single sample was obtained. The blood samples were centrifuged for 10 min at 1,600 g and at a temperature of 4° C. 10 min after drawing. The supernatant was transferred to labeled polypropylene tubes (2 tubes per sample) by pipetting and is further transferred to a deep-freezer for storing at a temperature of −20° C. (tolerance+5° C.) or lower.
  VLA-4 Measurements:
    Blood samples were obtained on visits on visits 2, 6, 7 and 8 for evaluating VLA-4 levels. 36 ml whole blood was needed for VLA-4 assay on lymphocytes.
  CD8+/CD4+ Measurements:
    For evaluation of CD8+/CD4+ cell count blood samples were assayed at visits 2, 6, 7 and 8 using the 36 ml blood samples obtained for VLA-4 assay.

Results

Primary Outcome Measure

Figure 2:
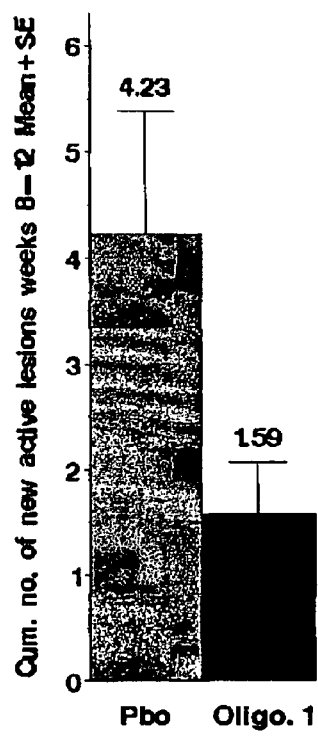
FIG. 2: (A and B) Illustrates the cumulative number of new active lesions measured by the MRI in the brain of RRMS patients on weeks 8 and 12, treated with OLIGONUCLEOTIDE 1 compared to placebo.
Figure 2:
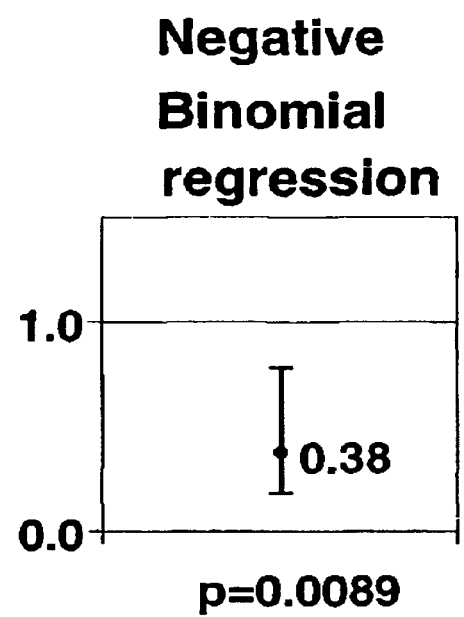
Figure 3:
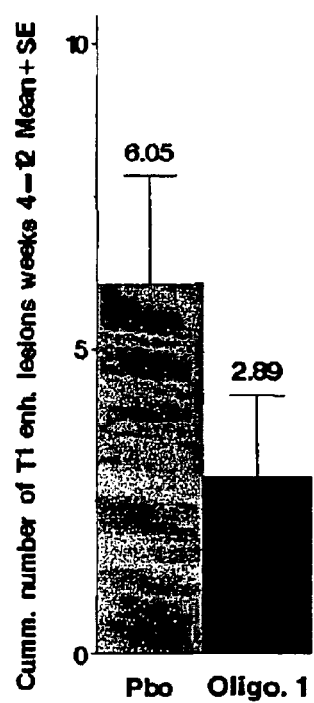
FIG. 3: (A, B and C) Illustrates the cumulative number of gadolinium-enhancing T1 lesions measured by the MRI in the brain of RRMS patients on weeks 4, 8 and 12, treated with OLIGONUCLEOTIDE 1 or receiving placebo. (C) OLIGONUCLEOTIDE 1 reduces the cumulative number of gadolinium-enhancing T1 lesions by 66.7%, p=0.002.
Figure 3:
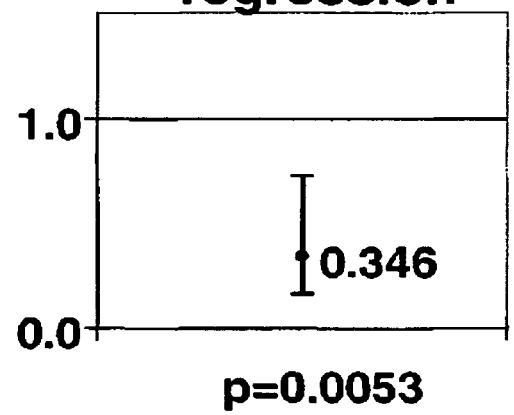
Figure 3:
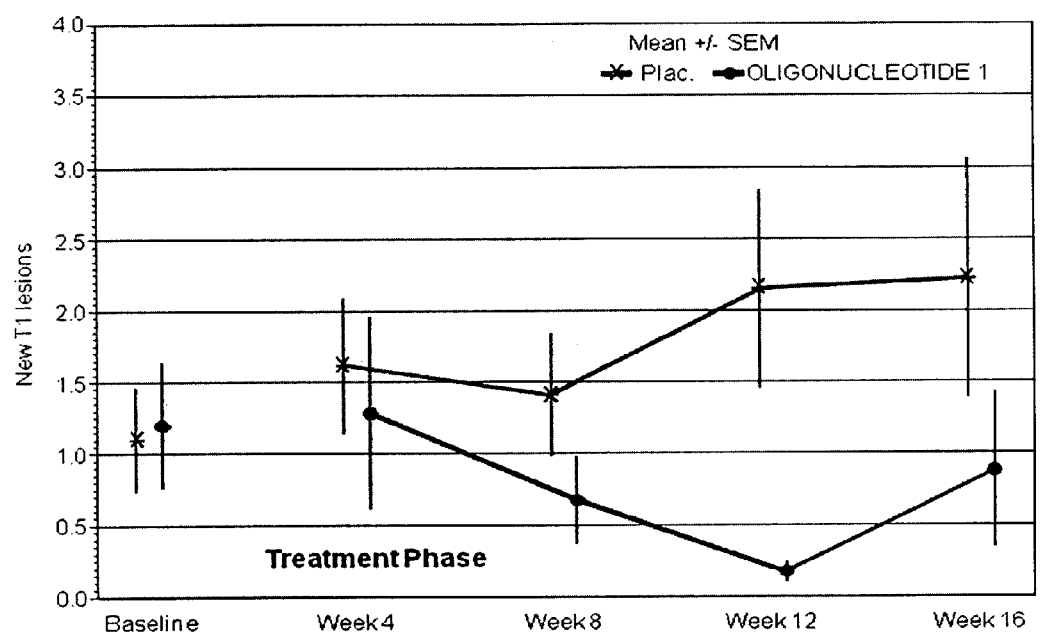
Figure 4:
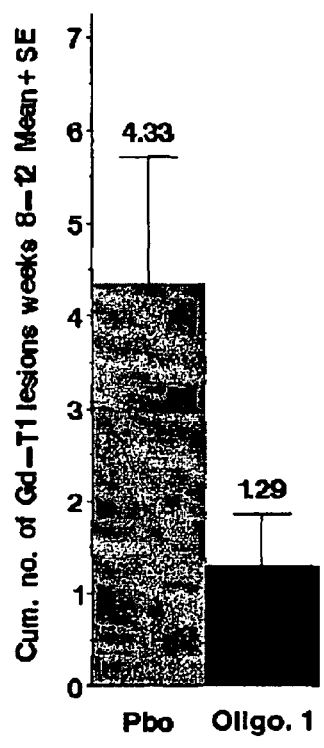
FIG. 4: (A and B) Illustrates the cumulative number of gadolinium-enhancing T1 lesions measured by the MRI in the brain of RRMS patients on weeks 8 and 12, treated with OLIGONUCLEOTIDE 1 or receiving placebo.
Figure 4:
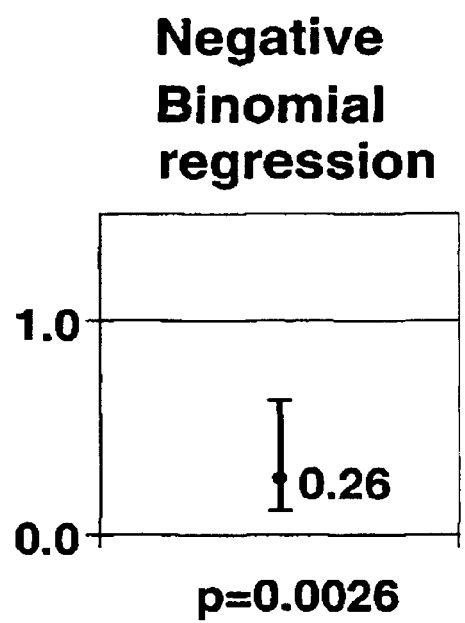
Figure 5:
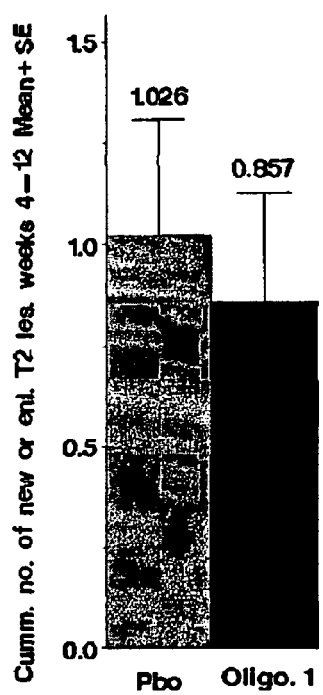
FIG. 5: (A and B) Illustrates the cumulative number of new or newly enlarging T2 lesions measured by the MRI in the brain of RRMS patients on weeks 4, 8 and 12, treated with OLIGONUCLEOTIDE 1 or receiving placebo.
Figure 5:
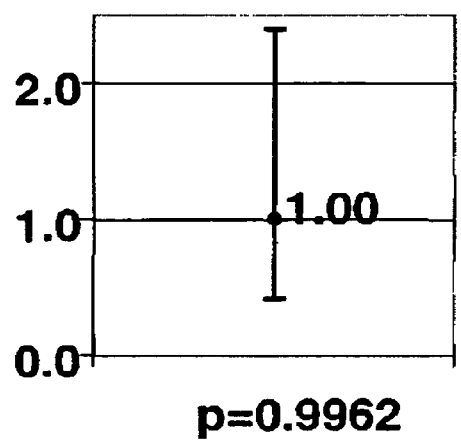
Figure 6:
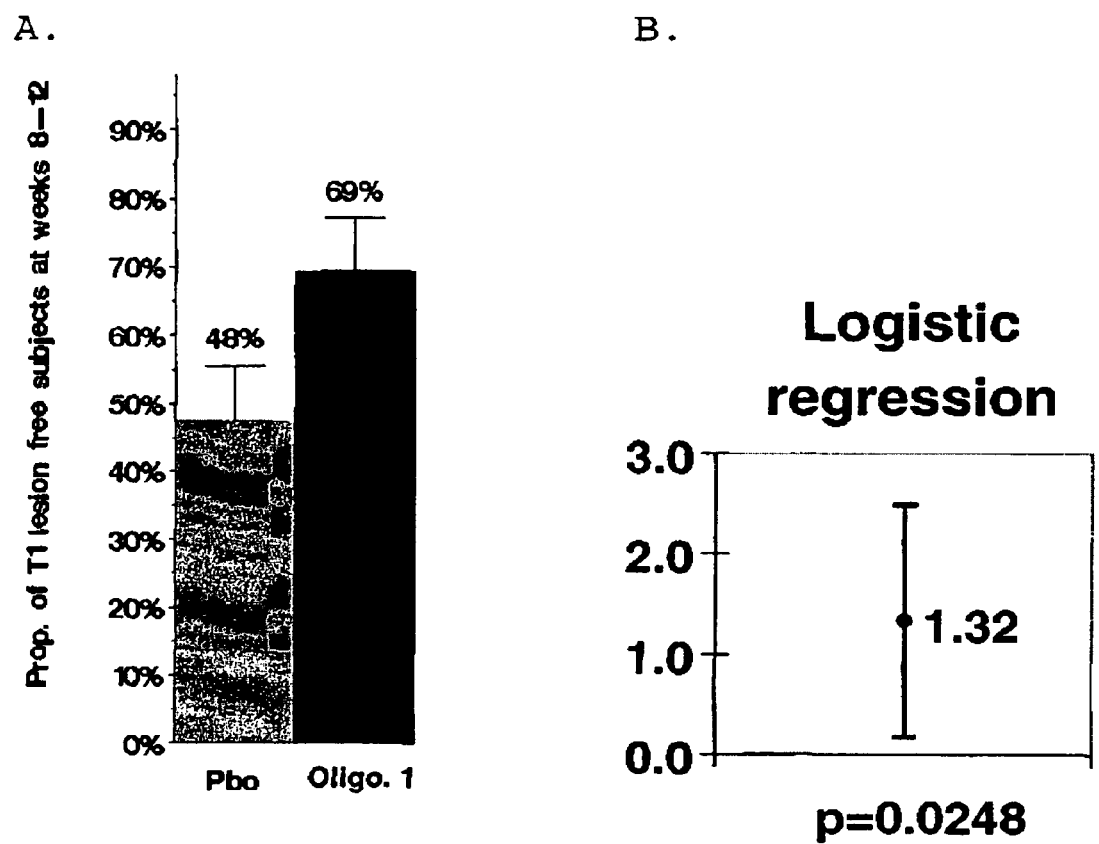
FIG. 6: (A and B) Illustrates the proportion of gadolinium-enhancing lesion free subjects on weeks 8 and 12 among RRMS patients treated with OLIGONUCLEOTIDE 1 compared to placebo.
Figure 8:
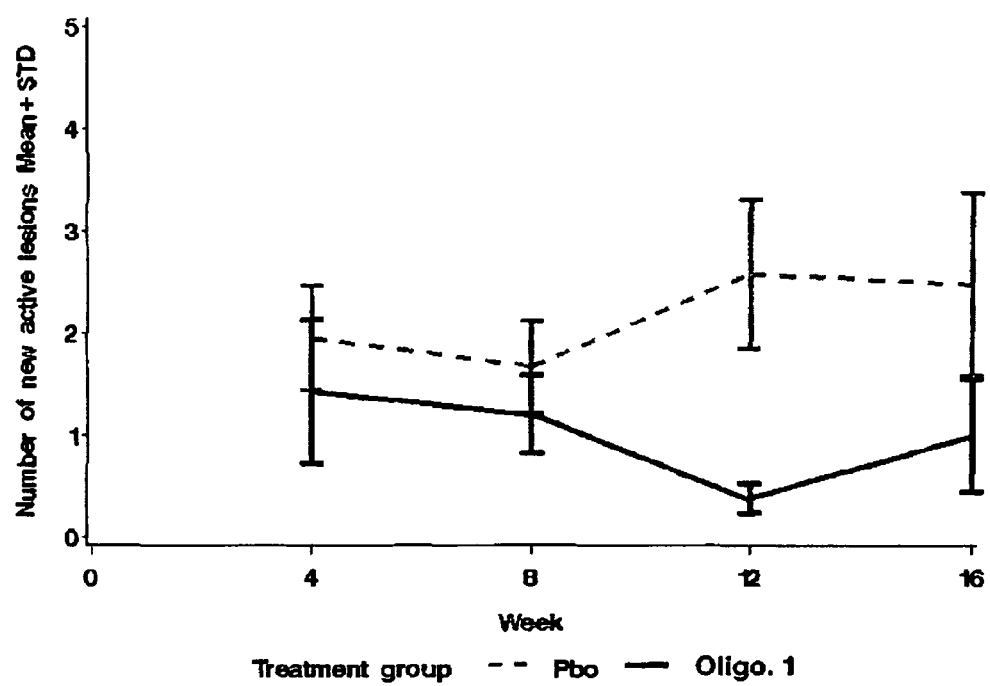
FIG. 8: Illustrates number of new active lesions over time in the treatment group compared to placebo.

Patients that had been receiving 200 mg OLIGONUCLEOTIDE 1 twice per week, by a subcutaneous route of administration during the study period, had showed a significant 54.4% reduction (p=0.01) in the cumulative number of new active lesions in the brain, including all lesions measured at weeks 4, 8 and 12 by the MRI, compared to patients that had been receiving placebo (FIG. 1). Moreover, patients that had been treated with OLIGONUCLEOTIDE 1, had showed 62% reduction (p=0.0089) in the cumulative number of new active lesions in the brain, measured at weeks 8 and 12 by the MRI, compared to the placebo group (FIG. 2) In addition, patients that had been treated with OLIGONUCLEOTIDE 1, had further showed 65% reduction (p=0.0053) and 74% reduction (p=0.0026) in the cumulative number of gadolinium-enhancing T1 lesions in the brain, measured at weeks 4, 8 and 12 or at weeks 8 and 12 by the MRI, compared to patients that had been receiving placebo respectively (FIG. 3-4). The cumulative number of new or newly enlarging T2 lesions in the brain measured by the MRI on weeks 4, 8 and 12 had been also reduced by the treatment with OLIGONUCLEOTIDE 1 (FIG. 5). Treatment with OLIGONUCLEOTIDE 1 had lead to 32% (p=0.0248) increase in the number of gadolinium-enhancing lesion-free subjects, measured at weeks 8 and 12 (FIG. 6) The maximal effect of OLIGONUCLEOTIDE 1 administration had been observed during the off-treatment cycle, at week 12 (FIG. 8). This finding points out high stability of OLIGONUCLEOTIDE 1 and thus further supports administration of less frequent dosing and/or lower doses of OLIGONUCLEOTIDE 1.

Conclusions

OLIGONUCLEOTIDE 1, in a placebo controlled, double-blind trial, was shown to be effective in preventing accumulation of new lesions detectable by MRI in the brain thereby slowing the progression of RRMS. This agent is a first example of an antisense oligonucleotide which has been proven to be effective and safe in the treatment of MS.

Secondary Outcome Measure

Figure 7:
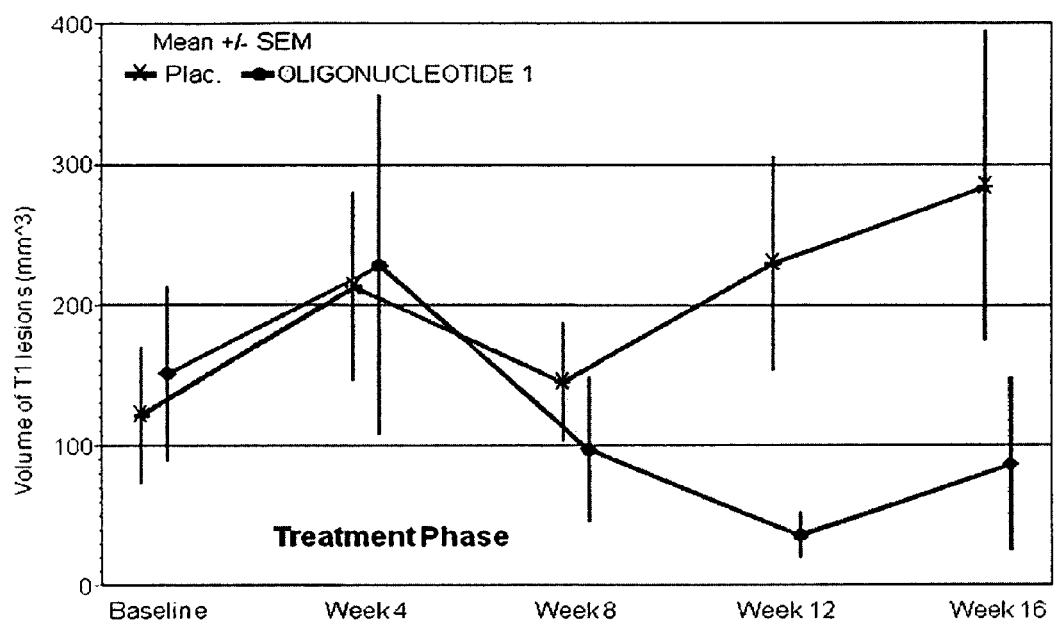
FIG. 7: Illustrates the trend in reduction of cumulative T1-gadolinium-enhancing lesion volume in the brain of RRMS patients over time in the treatment group compared to placebo.

The secondary endpoint of the study shows a cumulative decrease in the volume of gadolinium-enhancing lesions measured by MRI (to include all lesions from weeks 4, 8, and 12), corrected to the volume of gadolinium-enhancing lesions at the baseline, in the brain of patients that had been treated with 200 mg OLIGONUCLEOTIDE 1 twice per week by a subcutaneous route of administration by 84% compared to placebo group at week 12 (FIG. 7).

Additional Measures

Thrombocytopenia

Thrombocytopenia was one of the main safety concerns. This phenomenon was observed with first generation antisense oligonucleotides. During the study, decrease in platelet count was observed in all patients treated with oligonucleotide 1. 12 patients (33%) had a decrease below 150,000 anytime during the treatment; 6 patients (17%) had a clinically meaningful decrease below 100,000; 2 patients had been withdrawn from study. None of the patients had bleeding episodes or any other thrombocytopenia-related clinical symptoms. All subjects displayed recovery when off drug, indicating that the effect was rapidly reversible. Changing treatment regimen to less frequent dosing is contemplated to resolve this problem while maintaining the therapeutic benefits.

Pharmacokinetic Data

Figure 9:
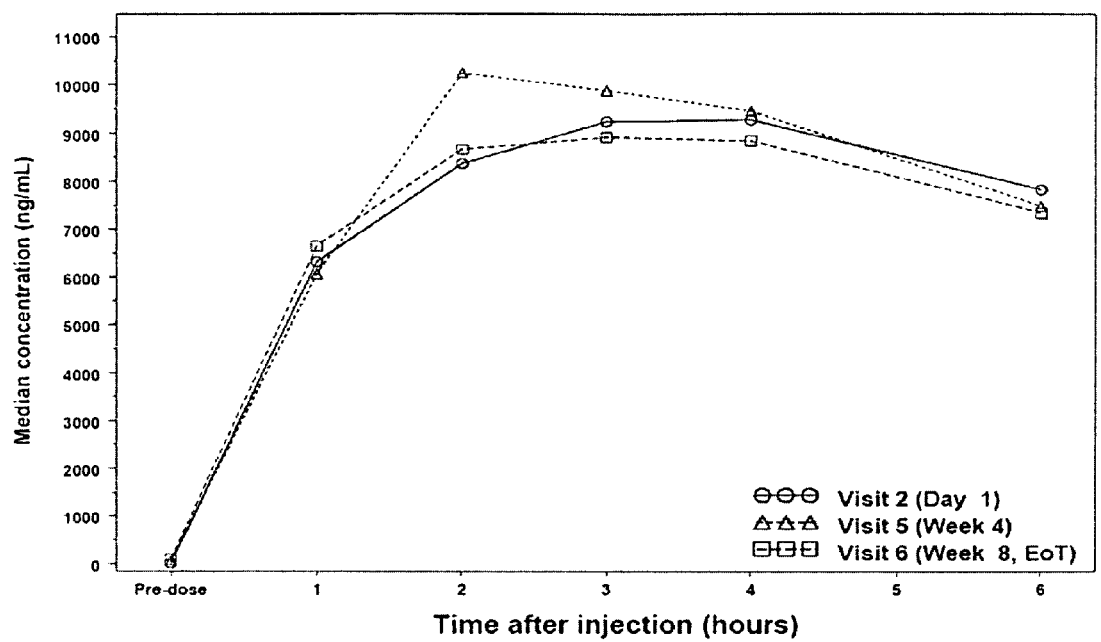
FIG. 9: Pharmacokinetics data Median profiles of OLIGONUCLEOTIDE 1 show no indication of accumulating peak or total plasma exposure levels from Day 1 to Week 8.

Median profiles of OLIGONUCLEOTIDE 1 show no indication of accumulating peak or total plasma exposure levels from Day 1 to Week 8 (FIG. 9 and Table III).

The increase in $C_{min}$ concentrations during the treatment phase suggests that OLIGONUCLEOTIDE 1 accumulates in tissue with multiple dose administrations. The decrease in $C_{min}$ concentrations during the follow-up phase suggests that the $t_{1/2}$ elimination is approximately 3 weeks.

TABLE III

| PK Parameters of OLIGONUCLEOTIDE 1 | |
| --- | --- |
| $C_{max}$ | 10157-10895 ng/mL (mean) |
| $T_{max}$ | 3 hrs (median) |
| $AUC_{last}$ | 46587-48521 h · ng/mL (mean) |

Example 2

Another clinical study is performed following substantially Example 1 except the administration of OLIGONUCLEOTIDE 1 is modified to the following three groups:

1) 200 mg per week;

2) 200 mg every 2 weeks; and 3) 400 mg every 4 weeks.

In this clinical trial similar effects to that of Example 1 are obtained with respect to cumulative number of new active lesions and the volume of gadolinium-enhancing lesions. In addition, a reduction in relapse rate and inhibition in the progression of disability are also observed. Furthermore, using the three types of administration, thrombocytopenia is limited and no patients are withdrawn from the trial due to a platelet count below 50,000 per microliter of blood. Most patients have a platelet count above 100,000 or 150,000 platelets per microliter of blood.

References:
1. McDonald W I, Compston A, Eden G et al., "Recommended Diagnostic Criteria for Multiple Sclerosis: Guidelines from the International Panel on the Diagnosis of Multiple Sclerosis"., Ann Neurol 2001; 50:121-127
2. CPMP—Committee for Proprietary Medicinal Products. "Note for Guidance on Good Clinical Practice." London, 1997, January; CPMP/ICH/135/95:1-58.
3. CPMP—Committee for Proprietary Medicinal Products. "Note for Guidance on Clinical Investigation of Medicinal Products for the Treatment of Multiple Sclerosis." London, 1999, Jul. 28; CPMP/EWP/561/98:1-10.
4. Medizinfo, Multiple Sklerose. Epidemiologie.
5. Johnson D, hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", J. Neuroimmunol. 1986 November; 13 (1):99-108.
6. Chou Y K, Bourdette D N, Offner H, Whitham R, Wang R Y, Hashim G A, Vandenbark A A., "Frequency of T cells specific for myelin basic protein and myelin proteolipid protein in blood and cerebrospinal fluid in multiple sclerosis.", J. Neuroimmunol. 1992 May; 38(1-2):105-13.
7. de Rosbo N K, Milo R, Lees M B, Burger D, Bernard C C, Ben-Nun A., "Reactivity to myelin antigens in multiple sclerosis. Peripheral blood lymphocytes respond predominantly to myelin oligodendrocyte glycoprotein.", J Clin Invest. 1993 December; 92(6):2602-8.
8. de Rosbo N K, Sen-Nun A., "T-cell responses to myelin antigens in multiple sclerosis; relevance of the predominant autoimmune reactivity to myelin oligodendrocyte glycoprotein.", J. Autoimmun. 1998 August; 11(4):287-99.
9. van Noort J M, van Sechel A C, Bajramovic J J, el Ouagmiri M, Polman C H, Lassmann H, Ravid R., "The small heat-shock protein alpha B-crystallin as candidate autoantigen in multiple sclerosis.", Nature 1995 Jun. 29; 375(6534):798-801.
10. Pelfrey C M, Tranquill L R, Vogt A B, McFarland H F., "T cell response to two immunodominant proteolipid protein (PLP) peptides in multiple sclerosis patients and healthy controls.", Mult Scler. 1996 April; 1(5):270-8.
11. Diaz-Villoslada P, Shih A, Shao L, Genain C P, Hauser S L., "Autoreactivity to myelin antigens: myelin/oligodendrocyte glycoprotein is a prevalent autoantigen." J. Neuroimmunol., 1999 Sep. 1; 99(1):36-43.
12. Pender M P, Csurhes P A, Greer J M, Mowat P D, Henderson R D, Cameron K D, Purdie D M, McCombe P A, Good M F., "Surges of increased T cell reactivity to an encephalitogenic region of myelin proteolipid protein occur more often in patients with multiple sclerosis than in healthy subjects.", J. Immunol. 2000 Nov. 1; 165(9):5322-31.
13. Rovira A', Leo'n A, "MR in the diagnosis and monitoring of multiple sclerosis: An overview.", Eur J Radiol (2008)
14. Van Oosten B W, Lai M, Hodgkinson S. Barkhof F et al., "Treatment of multiple sclerosis with the monoclonal anti-CD4 antibody cM-T412: results of a randomised, double-blind, placebo-controlled MR-monitored phase II trial.", Neurology. 1997; 49:351-357.
15. Paty D W, Hashimoto S A, Ebers G C., "Management of Multiple Sclerosis and Interpretation of Clinical Trials.", Multiple Sclerosis/editors, Paty. D W, Ebers G C, Philadelphia, 1998:457.
16. Kuang-Yu Jen & Alan M. Gewirtz, "Suppression of Gene Expression by Targeted Disruption of Messenger RNA.", Stem Cells 2000; 18; 307-319.
17. Helene, C. and J. J. Toulme, "Specific regulation of gene expression by antisense, sense and antigene nucleic acids.", Biochim Biophys Acta, 1990; 1049(2):99-125.
18. Cohen, J. S., "Antisense oligodeoxynucleotides as antiviral agents.", Antiviral Res, 1991; 16(2):121-33.
19. Calabretta, B., "Inhibition of protooncogene expression by antisense oligodeoxynucleotides: biological and therapeutic implications.", Cancer Res, 1991; 51(17):4505-10.
20. Crooke, S. T., "Progress toward oligonucleotide therapeutics: pharmacodynamic properties.", Faseb J, 1993; 7(6):533-9.
21. Crooke, S. T., "Therapeutic applications of oligonucleotides.", Annu Rev Pharmacol Toxicol, 1992; 32:329-76.
22. Steinman, L., "Blocking adhesion molecules as therapy for multiple sclerosis: natalizumab.", Nature Reviews Drug Discovery 4, 510-518 (June 2005)
23. Gary R. Cutter, Monika L. Baier, Richard A. Rudick, Diane L. Cookfair, Jill S. Fischer, John Petkau, Karl Syndulko, Brian G. Weinshenker, Jack P. Antel, Christian Confavreux, George W. Ellison, Fred Lublin, Aaron E. Miller, Stephen M. Rao, Stephen Reingold, Alan Thompson and Ernest Willoughby, "Development of a multiple sclerosis functional composite as a clinical trial outcome measure.", Brain 122:871-882, 1999.
24. Brex P A et al., "A longitudinal study of abnormalities on MAI and disability from multiple sclerosis", N Engl J Med 2002 Jan. 17, 346(3):158-64.
25. Frohman E M et al., "The utility of MRI in suspected MS: report of the Therapeutics and Technology Assessment Subcommittee of the American Academy of Neurology", Neurology, 2003, Sep. 9, 61(5):602-11.
26. The Merck Manual of Medical Information, Second Home Edition; Blood Disorders, Bleeding and Clotting Disorders. Last full review/revision May 2006 by Joel L. Moake, Md.

What is claimed is:

1. A method for decreasing or inhibiting the accumulation of new active brain lesions, or decreasing or inhibiting an increase in the volume of gadolinium-enhancing brain lesions in a human subject afflicted with multiple sclerosis, comprising periodically administering to the human subject a pharmaceutical composition comprising a pharmaceutically acceptable carrier and a therapeutically effective amount of an oligonucleotide having the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO: 1) wherein a) each of the 19 internucleotide linkages of the oligonucleotide is an O, O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C), or a pharmaceutically acceptable salt of the oligonucleotide, so as to thereby decrease or inhibit the accumulation of new active brain lesions, or decrease or inhibit an increase in the volume of gadolinium-enhancing brain lesions in a human subject afflicted with multiple sclerosis.

2. The method of claim 1, wherein the method inhibits progression of disability in the human subject or reduces relapse rate in the human subject.

3. The method of claim 1, wherein the periodic administration is twice per week.

4. The method claim 1, wherein the periodic administration is once per week.

5. The method claim 1, wherein the periodic administration is once every two weeks.

6. The method claim 1, wherein the periodic administration is once every three weeks.

7. The method claim 1, wherein the periodic administration is once every four weeks.

8. The method claim 1, wherein the periodic administration is once per month.

9. The method claim 1, wherein the amount effective to decrease or inhibit the accumulation of new active brain lesions, or decrease or inhibit the increase in the volume of gadolinium-enhancing brain lesions in the human subject is 50-400 mg.

10. The method claim 1, wherein the amount effective to decrease or inhibit the accumulation of new active brain lesions, or decrease or inhibit the increase in the volume of gadolinium-enhancing brain lesions in the human subject is 200 mg.

11. The method claim 1, wherein the amount effective to decrease or inhibit the accumulation of new active brain lesions, or decrease or inhibit the increase in the volume of gadolinium-enhancing brain lesions in the human subject is 200 mg, 400 mg, less than 400 mg, or 50 mg to less than 400 mg.

12. The method claim 1, wherein the average platelet count of the human subject is above 100,000 platelets per microliter of blood during the course of administration.

13. The method claim 1, wherein the average platelet count of the human subject is above 150,000 platelets per microliter of blood during the course of administration.

14. The method claim 1, wherein the administration is effective to provide a $C_{max}$ of the oligonucleotide in the plasma of the human subject of 10,000-11,000 ng/ml.

15. The method claim 1, wherein the pharmaceutical composition is administered subcutaneously.

16. The method claim 1, wherein the oligonucleotide is in the form of a sodium salt.

17. The method claim 1, wherein the oligonucleotide is in the form of a potassium salt.

18. The method claim 1, wherein the pharmaceutical carrier is WFI (water for injection) and the pharmaceutical composition is adjusted to pH 7.2-7.6.

19. The method of claim 12, wherein the pharmaceutical carrier is WFI (water for injection) and the pharmaceutical composition is adjusted to pH 7.4.

20. The method of claim 1, wherein the multiple sclerosis is primary progressive multiple sclerosis, secondary multiple sclerosis, or a relapsing form of multiple sclerosis.

21. The method of claim 1, wherein the amount effective to decrease or inhibit the accumulation of new active brain lesions, or decrease or inhibit the increase in the volume of gadolinium-enhancing brain lesions in the human subject is 400 mg once per week.

22. The method of claim 1, wherein the amount effective to decrease or inhibit the accumulation of new active brain lesions, or decrease or inhibit the increase in the volume of gadolinium-enhancing brain lesions in the human subject is 200 mg once per week.

23. The method of claim 1, wherein the amount effective to decrease or inhibit the accumulation of new active brain lesions, or decrease or inhibit the increase in the volume of gadolinium-enhancing brain lesions in the human subject is 200 mg once every two weeks.

24. The method of claim 1, wherein the amount effective to decrease or inhibit the accumulation of new active brain lesions, or decrease or inhibit the increase in the volume of gadolinium-enhancing brain lesions in the human subject is 400 mg once every four weeks.

25. The method of claim 1, further comprising reducing the level of VLA-4 in the blood of the human subject.

26. The method of claim 20, wherein the progression of disability is reduced by 15%-70% as measured by EDSS score relative to the progression of disability in a human subject afflicted primary progressive multiple sclerosis, secondary multiple sclerosis, or a relapsing form of multiple sclerosis no administered the pharmaceutical composition.

27. The method of claim 20, wherein the number of new active brain lesions detectable by MRI is 25%-80% lower than the number of new active brain lesions detectable by MRI in a human subject afflicted with primary progressive multiple sclerosis, secondary multiple sclerosis, or a relapsing form of multiple sclerosis not treated with the pharmaceutical composition.

28. The method of claim 20, wherein the number of new active brain lesions detectable by MRI is 50%-65% lower after 8 weeks of treatment than the number of new active brain lesions detectable by MRI in a human subject afflicted with primary progressive multiple sclerosis, secondary progressive multiple sclerosis, or a relapsing form of multiple sclerosis not treated with the pharmaceutical composition.

29. The method of claim 20, wherein the volume of gadolinium-enhancing brain lesions detectable by MRI is 25%-80% lower than the volume of gadolinium-enhancing brain lesions detectable by MRI in a human subject afflicted with primary progressive multiple sclerosis, secondary progressive multiple sclerosis, or a relapsing form of multiple sclerosis not treated with the pharmaceutical composition.

30. The method of claim 29, wherein the MRI method is selected from the group consisting of T2-weighted scanning, precontrast T1-weighted scanning, and post-gadolinium T1-weighted scanning.

31. The method of claim 28, wherein the MRI method is selected from the group consisting of T2-weighted scanning, precontrast T1 weighted scanning, and post-gadolinium T1-weighted scanning.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: artificial
<220> FEATURE:
<223> OTHER INFORMATION: Chemically synthesized
<220> FEATURE:
<221> NAME/KEY: modified ribonucleoside
<222> LOCATION: (1)..(1)
<223> OTHER INFORMATION: 2'-O-(2-methoxyethyl) ribose and 5-
      methylcytosine
<220> FEATURE:
```

```
<221> NAME/KEY: modified ribonucleoside
<222> LOCATION: (2)..(3)
<223> OTHER INFORMATION: 2'-O-(2-methoxyethyl) ribose
<220> FEATURE:
<221> NAME/KEY: 2'-deoxyribonucleoside
<222> LOCATION: (4)..(6)
<223> OTHER INFORMATION: 2'-deoxyribonucleosides
<220> FEATURE:
<221> NAME/KEY: modified ribonucleoside
<222> LOCATION: (7)..(7)
<223> OTHER INFORMATION: 2'-deoxyribonucleoside and 5-methylcytosine
<220> FEATURE:
<221> NAME/KEY: 2'-deoxyribonucleoside
<222> LOCATION: (8)..(12)
<223> OTHER INFORMATION: 2'-deoxyribonucleosides
<220> FEATURE:
<221> NAME/KEY: modified ribonucleoside
<222> LOCATION: (13)..(13)
<223> OTHER INFORMATION: 2'-O-(2-methoxyethyl) ribose
<220> FEATURE:
<221> NAME/KEY: modified ribonucleoside
<222> LOCATION: (14)..(15)
<223> OTHER INFORMATION: 2'-O-(2-methoxyethyl) ribose and 5-
      methylcytosine
<220> FEATURE:
<221> NAME/KEY: modified ribonucleoside
<222> LOCATION: (16)..(18)
<223> OTHER INFORMATION: 2'-O-(2-methoxyethyll) ribose
<220> FEATURE:
<221> NAME/KEY: modified ribonucleoside
<222> LOCATION: (19)..(19)
<223> OTHER INFORMATION: 2'-O-(2-methoxyethyl) ribose and 5-
      methylcytosine
<220> FEATURE:
<221> NAME/KEY: modified ribonucleoside
<222> LOCATION: (20)..(20)
<223> OTHER INFORMATION: 2'-O-(2-methoxyethyl) ribose

<400> SEQUENCE: 1
cugagtctgt ttccauucu                                              20
```